US010478435B2

(12) United States Patent
Stauderman et al.

(10) Patent No.: US 10,478,435 B2
(45) Date of Patent: Nov. 19, 2019

(54) USE OF CRAC CHANNEL INHIBITORS FOR THE TREATMENT OF STROKE AND TRAUMATIC BRAIN INJURY

(71) Applicants: CalciMedica, Inc., La Jolla, CA (US); The United States Government as Represented by the Department of Veterans Affairs, Washington, DC (US)

(72) Inventors: Kenneth Stauderman, San Diego, CA (US); Michael Dunn, La Jolla, CA (US); Sudarshan Hebbar, La Jolla, CA (US); Midori Yenari, San Francisco, CA (US); Rachid Kacimi, San Francisco, CA (US)

(73) Assignees: CALCIMEDICA, INC., La Jolla, CA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/751,098

(22) PCT Filed: Aug. 5, 2016

(86) PCT No.: PCT/US2016/045846
§ 371 (c)(1),
(2) Date: Feb. 7, 2018

(87) PCT Pub. No.: WO2017/027400
PCT Pub. Date: Feb. 16, 2017

(65) Prior Publication Data
US 2018/0235959 A1 Aug. 23, 2018

Related U.S. Application Data

(60) Provisional application No. 62/202,751, filed on Aug. 7, 2015.

(51) Int. Cl.
| | | |
|---|---|---|
| A61K 31/497 | (2006.01) |
| A61K 45/06 | (2006.01) |
| A61K 31/415 | (2006.01) |
| A61K 31/422 | (2006.01) |
| A61K 31/425 | (2006.01) |
| A61K 31/44 | (2006.01) |
| A61K 31/496 | (2006.01) |
| A61P 7/00 | (2006.01) |
| A61K 31/427 | (2006.01) |
| A61P 9/10 | (2006.01) |
| A61P 25/00 | (2006.01) |

(52) U.S. Cl.
CPC .......... *A61K 31/497* (2013.01); *A61K 31/415* (2013.01); *A61K 31/422* (2013.01); *A61K 31/425* (2013.01); *A61K 31/427* (2013.01); *A61K 31/44* (2013.01); *A61K 31/496* (2013.01); *A61K 45/06* (2013.01); *A61P 7/00* (2018.01); *A61P 9/10* (2018.01); *A61P 25/00* (2018.01)

(58) Field of Classification Search
CPC .. A61K 31/497; A61K 31/415; A61K 31/422; A61K 31/425; A61K 41/427; A61K 31/44; A61K 31/496; A61K 45/06
USPC .................................................. 514/255.05
See application file for complete search history.

(56) References Cited

U.S. PATENT DOCUMENTS

| | | |
|---|---|---|
| 6,348,480 B1 | 2/2002 | Kubota et al. |
| 6,506,747 B1 | 1/2003 | Betageri et al. |
| 6,958,339 B2 | 10/2005 | Kubota et al. |
| 7,709,518 B2 | 5/2010 | Chen et al. |
| 7,816,535 B2 | 10/2010 | Bohnert et al. |
| 8,030,336 B2 | 10/2011 | Burns et al. |
| 8,546,403 B2 | 10/2013 | Whitten et al. |
| 8,980,629 B2 | 3/2015 | Whitten et al. |
| 9,120,751 B2 | 9/2015 | Whitten et al. |
| 9,399,638 B2 | 7/2016 | Irlapati et al. |
| 10,106,529 B2 * | 10/2018 | Whitten ............... C07D 213/74 |
| 2001/0044445 A1 | 11/2001 | Bamaung et al. |
| 2002/0034728 A1 | 3/2002 | Normant et al. |
| 2006/0030567 A1 | 2/2006 | Ehrenfreund et al. |
| 2006/0100245 A1 | 5/2006 | Bakthavatchalam et al. |
| 2006/0199845 A1 | 9/2006 | Sun et al. |
| 2006/0235028 A1 | 10/2006 | Li et al. |

(Continued)

FOREIGN PATENT DOCUMENTS

| | | |
|---|---|---|
| JP | 2001080412 A | 3/2001 |
| JP | 2001522834 A | 11/2001 |

(Continued)

OTHER PUBLICATIONS

European Medicines Agency. Public summary of opinion on orphan designation N-(5-(6-chloro-2,2-difluorobenzo[d][1,3]dioxo1-5-yl)pyrazin-2-yl)-2-fluoro-6-methylbenzamide for the treatment of acute pancreatitis. Committee report [online]. (Dec. 13, 2016) [Retrieved on Feb. 26, 2018]. Retrieved from the Internet:<URL:http://www.ema.europa.eu/docs/en_GB/document_library/Orphan_designation/2016/12NV C500 217961.pdf> (5 pgs.).
Gomez-Puerta et al. Tyrosine kinase inhibitors for the treatment of rheumatoid arthritis. Curr Top Med Chem. 13(6):760-773 (2013).
PCT/US2018/015555 International Search Report and Written Opinion dated Apr. 4, 2018.
U.S. Appl. No. 14/805,292 Office Action dated Mar. 30, 2018.
Arthritis. http://en.wikipedia.org/wiki/Arthritis (1 pg.) (2014).
Baba et al. Coupling of STIM1 to store-operated Ca2+ entry through its constitutive and inducible movement in the endoplasmic reticulum. PNAS USA 103:16704-16709 (2006).

(Continued)

*Primary Examiner* — Yevgeny Valenrod
(74) *Attorney, Agent, or Firm* — Wilson Sonsini Goodrich & Rosati

(57) ABSTRACT

Described herein are methods of treatment of stroke and traumatic brain injury comprising administration of a CRAC channel inhibitor.

20 Claims, 4 Drawing Sheets

(56) References Cited

U.S. PATENT DOCUMENTS

| | | |
|---|---|---|
| 2007/0031814 A1 | 2/2007 | Roos et al. |
| 2007/0105867 A1 | 5/2007 | Chidambaram et al. |
| 2007/0249050 A1 | 10/2007 | Chen et al. |
| 2007/0249609 A1 | 10/2007 | Chen et al. |
| 2007/0254363 A1 | 11/2007 | Chen et al. |
| 2007/0254912 A1 | 11/2007 | Chen et al. |
| 2007/0254925 A1 | 11/2007 | Vo et al. |
| 2007/0254926 A1 | 11/2007 | Jiang et al. |
| 2008/0064874 A1 | 3/2008 | Dunkel et al. |
| 2008/0293092 A1 | 11/2008 | Stauderman et al. |
| 2009/0311720 A1 | 12/2009 | Roos et al. |
| 2010/0016598 A1 | 1/2010 | Valacchi et al. |
| 2010/0041762 A1 | 2/2010 | Bohnert et al. |
| 2010/0130510 A1 | 5/2010 | Chen et al. |
| 2010/0130522 A1 | 5/2010 | Jiang et al. |
| 2010/0152241 A1 | 6/2010 | Whitten |
| 2010/0273744 A1 | 10/2010 | Gore et al. |
| 2010/0286103 A1 | 11/2010 | Chen |
| 2010/0292252 A1 | 11/2010 | Chen |
| 2010/0311787 A1 | 12/2010 | Chen et al. |
| 2011/0015184 A1 | 1/2011 | Bohnert et al. |
| 2011/0052643 A1 | 3/2011 | Che et al. |
| 2011/0105447 A1 | 5/2011 | Muthuppalaniappan et al. |
| 2011/0112058 A1 | 5/2011 | Muthuppalaniappan et al. |
| 2011/0230536 A1 | 9/2011 | Whitten et al. |
| 2011/0305709 A1 | 12/2011 | Braun et al. |
| 2012/0035237 A1 | 2/2012 | Coe et al. |
| 2012/0053210 A1 | 3/2012 | Whitten et al. |
| 2012/0316185 A1 | 12/2012 | Beattie et al. |
| 2013/0252974 A1 | 9/2013 | Altenburger et al. |
| 2014/0256771 A1 | 9/2014 | Cao et al. |
| 2015/0322012 A1 | 11/2015 | Whitten et al. |
| 2018/0235958 A1 | 8/2018 | Velicelebi et al. |

FOREIGN PATENT DOCUMENTS

| | | |
|---|---|---|
| JP | 2003527324 A | 9/2003 |
| JP | 2006510737 A | 3/2006 |
| JP | 2011513332 A | 4/2011 |
| WO | WO-9806719 A1 | 2/1998 |
| WO | WO-9951580 A1 | 10/1999 |
| WO | WO-2004056774 A2 | 7/2004 |
| WO | WO-2005009539 A2 | 2/2005 |
| WO | WO-2005009954 A2 | 2/2005 |
| WO | WO-2006034402 A2 | 3/2006 |
| WO | WO-2006081389 A1 | 8/2006 |
| WO | WO-2006081391 A2 | 8/2006 |
| WO | WO-2006083477 A2 | 8/2006 |
| WO | WO-2006089177 A2 | 8/2006 |
| WO | WO-2007052123 A2 | 5/2007 |
| WO | WO-2007056341 A1 | 5/2007 |
| WO | WO-2007081804 A2 | 7/2007 |
| WO | WO-2007087429 A2 | 8/2007 |
| WO | WO-2007093542 A1 | 8/2007 |
| WO | WO-2007112093 A2 | 10/2007 |
| WO | WO-2007120600 A2 | 10/2007 |
| WO | WO-2008002576 A2 | 1/2008 |
| WO | WO-2008063504 A2 | 5/2008 |
| WO | WO-2009020642 A1 | 2/2009 |
| WO | WO-2009035818 A2 | 3/2009 |
| WO | WO-2010025295 A2 | 3/2010 |
| WO | WO-2010027875 A2 | 3/2010 |
| WO | WO-2010034011 A2 | 3/2010 |
| WO | WO-2010122089 A1 | 10/2010 |
| WO | WO-2011034962 A2 | 3/2011 |
| WO | WO-2011063277 A1 | 5/2011 |
| WO | WO-2011139489 A2 | 11/2011 |
| WO | WO-2011139765 A2 | 11/2011 |
| WO | WO-2012027710 A2 | 3/2012 |
| WO | WO-2012151355 A2 | 11/2012 |
| WO | WO-2012170931 A2 | 12/2012 |
| WO | WO-2012170951 A2 | 12/2012 |
| WO | WO-2013059666 A1 | 4/2013 |
| WO | WO-2013059677 A1 | 4/2013 |
| WO | WO-2013164769 A1 | 11/2013 |
| WO | WO-2014043715 A1 | 3/2014 |
| WO | WO-2014059333 A1 | 4/2014 |
| WO | WO-2016138472 A1 | 9/2016 |
| WO | WO-2017027400 A1 | 2/2017 |
| WO | WO-2018140796 A1 | 8/2018 |

OTHER PUBLICATIONS

Berridge. Inositol trisphosphate and calcium signalling. Nature 361:315-325 (1993).

Brayer et al. Alleles from chromosomes 1 and 3 of NOD mice combine to influence Sjögren's syndrome-like autoimmune exocrinopathy. J. Rheumatol. 27:1896-1904 (2000).

Chaplan et al. Quantitative assessment of tactile allodynia in the rat paw. J Neurosci Methods 53:55-63 (1994).

Cho. Recent Advances in Oral Prodrug Discovery. Annual Reports in Medicinal Chemistry 41:395-407 (2006).

Churchill et al. Imaging of intracellular calcium stores in single permeabilized lens cells. Am. J. Physiol. 276:C426-434 (1999).

Colitis. http://www.healthline.com/health/ulterative-colitis-take-control-can-it-be-cured? (3 pgs) (2014).

Dargie et al. Comparison of Ca2+ mobilizing activities of cyclic ADP-ribose and inositol trisphosphate. Cell Regul. 1:279-290 (1990).

Fagan et al. Regulation of the Ca2+-inhibitable adenylyl cyclase type VI by capacitative Ca2+ entry requires localization in cholesterol-rich domains. J Biol Chem 275(34):26530-26537 (Aug. 25, 2000).

Fedorak et al. A novel colon-specific steroid prodrug enhances sodium chloride absorption in rat colitis. Am. J. Physiol. 269:G210-218 (1995).

Feske et al. A Mutation in Orai1 Causes Immune Deficiency by Abrogating CRAC Channel Function. Nature 441:179-185 (2006).

Funaba et al. Degranulation in RBL-2H3 cells: regulation by calmodulin pathway. Cell Biol Int 27:879-885 (2003).

Gerasimenko et al. Inositol trisphosphate and cyclic ADP-ribose-mediated release of Ca2+ from single isolated pancreatic zymogen granules. Cell 84:473-480 (1996).

Gompertz et al. Bedside index for severity in acute pancreatitis (BISAP) score as predictor of clinical outcome in acute pancreatitis: retrospective review of 128 patients. Rev Med Chil 140(8):977-983 (2012).

Griffiths et al. Genetic analysis of collagen-induced arthritis in rats: a polygenic model for rheumatoid arthritis predicts a common framework of cross-species inflammatory/autoimmune disease loci. Immunol. Rev. 184:172-183 (2001).

Gromoda et al. Cyclic ADP-ribose and inositol 1,4,5-triphosphate mobilizes Ca2+ from distinct intracellular pools in permeabilized lacrimal acinar cells. FEBS Lett. 360:303-306 (1995).

Guse et al. Regulation of calcium signalling in T lymphocytes by the second messenger cyclic ADP-ribose. Nature 398:70-73 (1999).

Hochhaus et al. A selective HPLC/RIA for dexamethasone and its prodrug dexamethasone-21-sulphobenzoate sodium in biological fluids. Biomed. Chrom. 6:283-286 (1992).

Hofer et al. Free [Ca2+] dynamics measured in agonist-sensitive stores of single living intact cells: a new look at the refilling process. EMBO J. 17:1986-1995 (1998).

Huang et al. STIM1 carboxyl-terminus activates native SOC, Icrac and TRPC1 channels. Nature Cell Biology 8(9):1003-1010 (2006).

Humbles et al. The murine CCR3 receptor regulates both the role of eosinophils and mast cells in allergen-induced airway inflammation and hyperresponsiveness. PNAS USA 99:1479-1484 (2002).

Humphreys-Beher et al. New concepts for the development of autoimmune exocrinopathy derived from studies with the NOD mouse model. Arch. Oral Biol. 44( Suppl 1):S21-25 (1999).

Jefferson et al. Experimental mesangial proliferative glomerulonephritis (the anti-Thy-1.1 model). J. Nephrol. 12:297-307 (1999).

Karlsson et al. Pulmonary-Allergy, Dermatological, Gastrointestinal & Arthiritis Phosphodiesterase 4 Inhibitors for the treatment of asthma. Exp. Opin. Their Patents. 7(9):989-1003 (1997).

Larsen et al. Prodrug forms for the sulfonamide group. I. Evaluation of N-acyl derivatives, N-sulfonylaminedes, N-sulfonylsulfilimines and sulfonylureas as possible prodrug derivatives. Int. J. Pharmaceutics 37:87-95 (1987).

(56) References Cited

OTHER PUBLICATIONS

Larsen et al. Prodrug forms for the sulfonamide group. II. water-soluble amino acid derivatives of N-methylsulfonylaminades as possible prodrug derivatives. Int'l J of Pharmaceutics 47:103-110 (1988).
Lewis. Calcium Signaling Mechanisms in T Lymphocytes. Annu Rev Immunol 19:497-521 (2001).
Liou et al. STIM is a Ca2+ sensor essential for Ca2+-store-depletion-triggered Ca2+ influx. Curr. Biol. 15(13):1235-1241 (2005).
Luik et al. The elementary unit of store-operated Ca2+ entry: local activation of CRAC channels by STIM1 at ER-plasma membrane junctions. J. Cell Biol. 174:815-825 (2006).
Luo et al. Upregulation of dorsal root ganglion (alpha)2(delta) calcium channel subunit and its correlation with allodynia in spinal nerve-injured rats. J. Neurosci 21:1868-1875 (2001).
Macian et al. Transcriptional mechanisms underlying lymphocyte tolerance. Cell 109(6):719-731 (Jun. 14, 2002).
Manji et al. STIM1: a novel phosphoprotein located at the cell surface. Biochim Biophys Acta. 1481(1):147-155 (2000).
McLeod et al. A glucocorticoid prodrug facilitates normal mucosal function in rat colitis without adrenal suppression. Gastroenterol 106:405-413 (1994).
Mercer et al. Large store-operated calcium selective currents due to co-expression of Orai1 or Orai2 with the intracellular calcium sensor, Stim1. JBC 281:24979-24990 (2006).
Millar et al. Functional expression of a cloned *Drosophila* muscarinic acetylcholine receptor in a stable *Drosophila* cell line. Exp. Biol. 198:1843-1850 (1995).
Miller et al. Histone deacetylase inhibitors. Med. Chem. 46(24):5097-5116 (2003).
Miyawaki et al. Fluorescent indicators for Ca2+ based on green fluorescent proteins and calmodulin. Nature 388(6645):882-887 (Aug. 28, 1997).
Multiple Sclerosis Prevention. Retrieved from http://www.webmd.com/multiple-sclerosis/tc/multiple-sclerosis-ms-prevention (3 pgs.) (2017).
Multiple Sclerosis Treatment. Retrieved from http://www.webmd.com/multiple-sclerosis/tc/multiple-sclerosis-ms-medications#1 (4 pgs) (2017).
Nogrady. Medicinal Chemistry A Biochemical Approach, Oxford University Press, New York, pp. 388-392 (1985).
Nunez et al. Cell proliferation depends on mitochondrial Ca2+ uptake: inhibition by salicylate. J Physiol. 571(Pt 1):57-73 (Feb. 15, 2006/ Epub Dec. 8, 2005).
Papachristou et al. Comparison of BISAP, Ranson's, APACHE-II, and CTSI scores in predicting organ failure, complications, and mortality in acute pancreatitis. Am J Gastroenterol. 105(2):435-441 (2010).
Parekh et al. Store Depletion and Calcium Influx. Physiol Rev 77(4):901-930 (1997).
Parekh et al. Store-Operated Calcium Channels. Physiol Rev 85:757-810 (2005).
Patani et al. Bioisosterism: A Rational Approach in Drug Design. Chem. Rev. 96:3147-3176 (1996).
Patterson et al. Phospholipase C-γ is Required for Agonist-Induced Ca2+ Entry. Cell 111(4):529-541 (2002).
PCT/US2011/031992 International Preliminary Report on Patentability dated Nov. 8, 2012.
PCT/US2011/031992 International Search Report dated Dec. 7, 2011.
PCT/US2016/019924 International Preliminary Report on Patentability dated Sep. 8, 2017.
PCT/US2016/019924 International Search Report and Written Opinion dated Jul. 8, 2016.
PCT/US2016/045846 International Preliminary Report on Patentability dated Feb. 22, 2018.
PCT/US2016/045846 International Search Report and Written Opinion dated Oct. 24, 2016.
Prakriya et al. Store-operated calcium channels: properties, functions and the search for a molecular mechanism. Molecular and Cellular Insights into Ion Channel Biology 32:121-140 (2004).
Putney et al. A model for receptor-regulated calcium entry. Cell Calcium. 7(1):1-12 (1986).
Putney et al. The signal for capacitative calcium entry. Cell 75(2):199-201 (1993).
Rao et al. Transcription factors of the NFAT family: regulation and function. Annu Rev Immunol. 15:707-747 (1997).
Roos et al. STIM1, an essential and conserved component of store-operated Ca2+ channel function. J Cell Biol 169(3):435-445 (2005).
Rooseboom et al. Enzyme-catalyzed activation of anticancer prodrugs. Pharmacological Reviews 56:53-102 (2004).
Rudensky et al. FOXP3 and NFAT: partners in tolerance. Cell 126(2):253-256 (2006).
Saulnier et al. An Efficient Method for the Synthesis of Guanidino Prodrugs. Bioorg Med Chem Lett 4(16):1985-1990 (1994).
Silverman. Chapter 8: Prodrugs and Drug Delivery Systems. The Organic Chemistry of Drug Design and Drug Action, Academic Press, Inc., San Diego (pp. 352-401) (1992).
Sinkula et al. Rationale for design of biologically reversible drug derivatives: prodrugs. J. Pharm. Sci. 64:181-210 (1975).
Spassova et al. STIM1 has a plasma membrane role in the activation of store-operated Ca(2+) channels. PNAS USA 103:4040-4045 (2006).
Stathopulos et al. Stored Ca2+ depletion-induced oligomerization of stromal interaction molecule 1 (STIM1) via the EF-SAM region: An initiation mechanism for capacitive Ca2+ entry. J. Biol. Chem. 281:35855-35862 (2006).
Streb et al. Release of Ca2+ from a nonmitochondrial intracellular store in pancreatic acinar cells by inositol-1,4,5-trisphosphate. Nature 306:67-69 (1983).
Trevilyan et al. Potent inhibition of NFAT activation and T cell cytokine production by novel low molecular weight pyrazole compounds. J Biol Chem. 276(51):48118-48126 (2001).
U.S. Appl. No. 13/085,324 Office Action dated Feb. 8, 2013.
U.S. Appl. No. 13/969,401 Office Action dated Dec. 10, 2014.
U.S. Appl. No. 13/969,401 Office Action dated Jul. 8, 2014.
U.S. Appl. No. 13/969,401 Office Action dated Mar. 17, 2014.
U.S. Appl. No. 13/975,238 Office Action dated Jan. 27, 2014.
U.S. Appl. No. 13/975,238 Office Action dated Jun. 9, 2014.
U.S. Appl. No. 14/805,292 Office Action dated Aug. 21, 2017.
U.S. Appl. No. 14/805,292 Office Action dated Feb. 6, 2017.
Vig et al. CRACM1 is a plasma membrane protein essential for store-operated Ca2+ entry. Science 312(5777):1220-1223 (2006).
Vig et al. CRACM1 Multimers Form the Ion-Selective Pore of the CRAC Channel. Current Biology 16:2073-2079 (2006).
Williams et al. Identification and characterization of the STIM (stromal interaction molecule) gene family: coding for a novel class of transmembrane proteins. Biochem. J. 357:673-685 (2001).
Winslow et al. Calcium Signalling in Lymphocytes. Current Opinion in Immunology 16:299-307 (2003).
Wu et al. Ca2+ store depletion causes STIM1 to accumulate in ER regions closely associated with the plasma membrane. J Cell Biol 174(6):803-813 (2006).
Wu et al. FOXP3 controls regulatory T cell function through cooperation with NFAT. Cell 126(2):375-387 (Jul. 28, 2006).
Wu et al. The early prediction of mortality in acute pancreatitis: a large population-based study. Gut 57(12):1698-1703 (2008).
Xu et al. Aggregation of STIM1 underneath the plasma membrane induces clustering of Orai1. Biochem. Biophys. Res. Commun. 350:969-976 (2006).
Yagodin et al. Functional characterization of thapsigargin and agonist-insensitive acidic Ca2+ stores in *Drosophila melanogaster* S2 cell lines. Cell Calcium 25:429-438 (1999).
Yagodin et al. Thapsigargin and receptor-mediated activation of Drosophila TRPL channels stably expressed in a *Drosophila* S2 cell line. Cell Calcium 23:219-228 (1998).
Yeromin et al. Molecular identification of the CRAC channel by altered ion selectivity in a mutant of Orai. Nature 443:226-229 (2006).

(56) References Cited

OTHER PUBLICATIONS

Yu et al. Rapid turnover of calcium in the endoplasmic reticulum during signaling. Studies with cameleon calcium indicators. J. Biol. Chem. 275:23648-23653 (2000).
Zhang et al. Genome Wide RNAi Screen of Ca2+ influx identifies Genes that Regulate Ca2+ Channel Activity. PNAS USA 103(4):9357-9362 (2006).
Zhang et al. STIM1 is a Ca2+ sensor that activates CRAC channels and migrates from the Ca2+ store to the plasma membrane. Nature 437(7060):902-905 (2005).
Derler et al. The action of selective CRAC channel blockers is affected by the Orai pore geometry. Cell Calcium 53(2):139-151 (2013).
Gerasimenko et al. Ca2+ release-activated Ca2+ channel blockade as a potential tool in antipancreatitis therapy. PNAS USA 110(32):13186-13191 (2013).
U.S. Appl. No. 14/805,292 Office Action dated Oct. 18, 2018.
Wen et al. Orail inhibition prevents calcium toxicity and acute pancreatitis. Pancreatology 3.14 Supp 1:S100-S101 (2014).
Frick. The role of calcium in acute pancreatitis. Surgery 152(3 Suppl 1):S157-S163 (2012).
U.S. Appl. No. 15/553,531 Office Action dated Aug. 13, 2019.

\* cited by examiner

New CM-D dose reponse on TLR3 agonist activates NO

USE OF CRAC CHANNEL INHIBITORS FOR THE TREATMENT OF STROKE AND TRAUMATIC BRAIN INJURY

CROSS REFERENCE

This application is filed pursuant to 35 U. SC. § 371 as a United States National Phase Application of International Application No. PCT/US2016/045846, filed Aug. 5, 2016, which claims the benefit of U.S. provisional patent application Ser. No. 62/202,751, filed Aug. 7, 2015, each of which is herein incorporated by reference in its entirety.

BACKGROUND OF THE INVENTION

Calcium plays a vital role in cell function and survival. For example, calcium is a key element in the transduction of signals into and within cells. Cellular responses to growth factors, neurotransmitters, hormones and a variety of other signal molecules are initiated through calcium-dependent processes.

Virtually all cell types depend in some manner upon the generation of cytoplasmic $Ca^{2+}$ signals to regulate cell function, or to trigger specific responses. Cytosolic $Ca^{2+}$ signals control a wide array of cellular functions ranging from short-term responses such as contraction and secretion to longer-term regulation of cell growth and proliferation. Usually, these signals involve some combination of release of $Ca^{2+}$ from intracellular stores, such as the endoplasmic reticulum (ER), and influx of $Ca^{2+}$ across the plasma membrane. In one example, cell activation begins with an agonist binding to a surface membrane receptor, which is coupled to phospholipase C (PLC) through a G-protein mechanism. PLC activation leads to the production of inositol 1,4,5-triphosphate ($IP_3$), which in turn activates the $IP_3$ receptor causing release of $Ca^{2+}$ from the ER. The fall in ER $Ca^{2+}$ then signals to activate plasma membrane store-operated calcium (SOC) channels.

Store-operated calcium (SOC) influx is a process in cellular physiology that controls such diverse functions such as, but not limited to, refilling of intracellular $Ca^{2+}$ stores (Putney et al. *Cell,* 75, 199-201, 1993), activation of enzymatic activity (Fagan et al., *J. Biol. Chem.* 275:26530-26537, 2000), gene transcription (Lewis, *Annu. Rev. Immunol.* 19:497-521, 2001), cell proliferation (Nunez et al., *J. Physiol.* 571.1, 57-73, 2006), and release of cytokines (Winslow et al., *Curr. Opin. Immunol.* 15:299-307, 2003). In some nonexcitable cells, e.g., blood cells, immune cells, hematopoietic cells, T lymphocytes and mast cells, SOC influx occurs through calcium release-activated calcium (CRAC) channels, a type of SOC channel.

The calcium influx mechanism has been referred to as store-operated calcium entry (SOCE). Stromal interaction molecule (STIM) proteins are an essential component of SOC channel function, serving as the sensors for detecting the depletion of calcium from intracellular stores and for activating SOC channels.

SUMMARY OF THE INVENTION

Provided herein are methods for treating stroke or traumatic brain injury in an individual in need thereof comprising administering to the individual a therapeutically effective amount of a compound having the structure of Formula (I), (II), or (III). In one aspect, compounds of Formula (I), (II), or (III) inhibit CRAC channel activity. In one aspect, compounds of Formula (I), (II), or (III) modulate intracellular calcium by inhibition of store operated calcium channel activity. In one aspect, compounds of Formula (I), (II), or (III) modulate intracellular calcium by preventing the activity of activated store operated calcium channel complexes. In one aspect, compounds of Formula (I), (II), or (III) inhibit activation of store operated channels. In one aspect, compounds of Formula (I), (II), or (III) inhibit activation of calcium-release activated calcium channels. In one aspect, compounds of Formula (I), (II), or (III) modulate an activity of, modulate an interaction of, or modulate the level of, or distribution of, or bind to, or interact with at least one protein of the SOC channel complex. In one aspect, compounds of Formula (I), (II), or (III) modulate an activity of, modulate an interaction of, or modulate the level of, or distribution of, or bind to, or interact with at least one protein of the CRAC channel complex.

In one aspect, described herein is a method for treating stroke or traumatic brain injury in an individual in need thereof comprising administering to the individual a therapeutically effective amount of a compound having the structure of Formula (I):

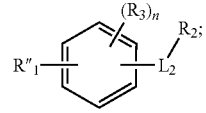

Formula (I)

wherein:
$R''_1$ is

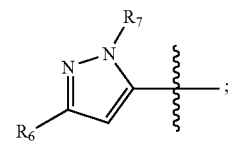

$L_2$ is —NH—C(=O)—, or —C(=O)NH—;
$R_2$ is phenyl or pyridyl; wherein phenyl or pyridyl is optionally substituted with at least one $R_3$;
$R_3$ is independently selected from F, Cl, Br, I, —CN, —$NO_2$, —OH, —$OCF_3$, —$OR_5$, and —$N(R_5)_2$;
n is an integer selected from 1-4;
each $R_5$ is independently selected from $C_1$-$C_6$alkyl, and $C_1$-$C_6$haloalkyl;
$R_7$ is $C_1$-$C_6$alkyl; and
$R_6$ is selected from F, Cl, Br, I, —CN, —$NO_2$, —OH, —$CF_3$, —$OCF_3$, —$OR_5$, $C_1$-$C_6$alkyl, $C_3$-$C_8$cycloalkyl, and $C_1$-$C_6$haloalkyl;
or a pharmaceutically acceptable salt or pharmaceutically acceptable solvate thereof.

In some embodiments is a method for treating stroke or traumatic brain injury in an individual in need thereof comprising administering to the individual a therapeutically effective amount of a compound having the structure of Formula (IA):

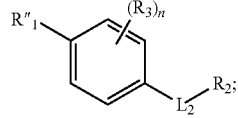

Formula (IA)

In some embodiments is a method wherein $L_2$ is —NH—C(=O)—. In some embodiments is a method wherein $R_2$ is phenyl optionally substituted with at least one $R_3$. In some embodiments is a method wherein $R_2$ is phenyl substituted with at least one $R_3$ selected from F, Cl, Br, I, —CN, —OH, —OCF$_3$, —OR$_5$, and —N(R$_5$)$_2$. In some embodiments is a method wherein $R_6$ is selected from —CF$_3$, —OCF$_3$, —OR$_5$, $C_1$-$C_6$alkyl, and $C_3$-$C_8$cycloalkyl. In some embodiments is a method wherein $R_6$ is —CF$_3$ and $R_7$ is —CH$_3$. In some embodiments is a method wherein $R_6$ is —CF$_3$ and $R_7$ is —CH$_2$CH$_3$. In some embodiments is a method wherein n is 1. In some embodiments is a method wherein $R_3$ is fluorine. In some embodiments is a method wherein $R_2$ is phenyl substituted with at least 2 F substituents. In some embodiments is a method wherein $R_2$ is phenyl substituted with at least 3 F substituents. In some embodiments is a method wherein $R_2$ is pyridyl. In some embodiments is a method wherein $R_2$ is pyridyl substituted with at least one $R_3$ selected from F, Cl, Br, —OH, —CN, —OCF$_3$, —OR$_5$, and —N(R$_5$)$_2$. In some embodiments is a method wherein $R_2$ is pyridyl substituted with at least one fluorine.

In another aspect, described herein is a method for treating stroke or traumatic brain injury in an individual in need thereof comprising administering to the individual a therapeutically effective amount of a compound having the structure of Formula (II):

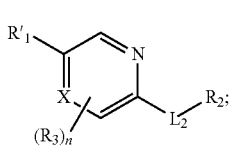

Formula (II)

wherein:
$R'_1$ is

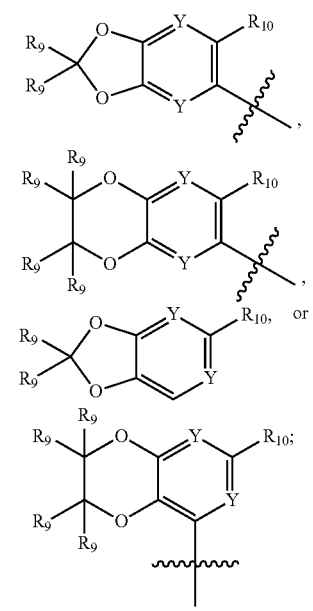

$L_2$ is —NH—C(=O)—, or —C(=O)NH—;
X is CR$_3$ or N;
Y is independently selected from CR$_9$ or N;

$R_2$ is $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, $C_1$-$C_4$alkyleneC$_2$-$C_8$heterocycloalkyl, aryl, heteroaryl, fused aryl or fused heteroaryl; wherein $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, $C_1$-$C_4$alkyleneC$_2$-$C_8$heterocycloalkyl, aryl, heteroaryl, fused aryl or fused heteroaryl is optionally substituted with at least one $R_3$;

$R_3$ is independently selected from H, F, D, Cl, Br, I, —CN, —NO$_2$, —OH, —CF$_3$, —OCF$_3$, —OR$_5$, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, optionally substituted aryl, optionally substituted O-aryl, optionally substituted heteroaryl, n is an integer selected from 0-2;

$R_9$ is independently selected from H, D, halogen, $C_1$-$C_6$alkyl, $C_1$-$C_6$haloalkyl, —OR$_5$, —OCF$_3$, $C_1$-$C_6$ carbonylalkyl, or —CF$_3$; or two $R_9$ attached to the same carbon atom form an oxetane ring;

$R_{10}$ is selected from halogen, $C_1$-$C_6$alkyl, $C_1$-$C_6$haloalkyl, —OR$_5$, —OCF$_3$, $C_1$-$C_6$ carbonylalkyl, or —CF$_3$;

$R_5$ is independently selected from H, $C_1$-$C_6$alkyl, $C_1$-$C_6$haloalkyl, $C_3$-$C_8$cycloalkyl, phenyl, and benzyl;

or a pharmaceutically acceptable salt, or pharmaceutically acceptable solvate thereof.

In some embodiments is a method wherein X is CH. In some embodiments is a method wherein X is N. In some embodiments is a method wherein $R'_1$ is

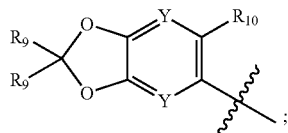

and Y is CH. In some embodiments is a method wherein $R_2$ is phenyl optionally substituted with at least one $R_3$. In some embodiments is a method wherein $R_2$ is phenyl substituted with at least one $R_3$ selected from Cl, Br, F, I, CF$_3$, $C_1$-$C_6$alkyl, or OC$_1$-$C_6$alkyl. In some embodiments is a method wherein $R_2$ is phenyl substituted with at least one $R_3$ selected from Cl, F, and CH$_3$. In some embodiments is a method wherein $R_2$ is phenyl substituted with at least one F. In some embodiments is a method wherein at least one $R_9$ is halogen. In some embodiments is a method wherein $R'_1$ is

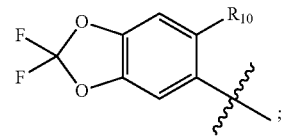

and n is 0. In some embodiments is a method wherein $R_{10}$ is halogen or $C_1$-$C_6$alkyl. In some embodiments is a method wherein $R_{10}$ is Cl. In some embodiments is a method wherein $R_{10}$ is —CH$_3$. In some embodiments is a method wherein $R_{10}$ is —CH$_2$CH$_3$. In some embodiments is a method wherein $R_2$ is phenyl substituted with two $R_3$, wherein one $R_3$ is F and one $R_3$ is CH$_3$. In some embodiments is a method wherein $R_2$ is phenyl substituted with two $R_3$, wherein one $R_3$ is F and one $R_3$ is Cl. In some embodiments is a method wherein $R_2$ is phenyl substituted with two $R_3$, wherein each $R_3$ is F. In some embodiments is a method wherein $R_2$ is phenyl substituted with three $R_3$, wherein each $R_3$ is F. In some embodiments is a method wherein $R_2$ is heteroaryl substituted with at least one $R_3$. In some embodiments is a method wherein $R_2$ is heteroaryl selected from pyridyl, pyrimidyl, pyridazinyl, pyrazinyl, thienyl, furyl, pyranyl, thiadiazolyl, pyrazolyl, imidazolyl, thiazolyl, isothiazolyl, oxazolyl, isoxazolyl, indolyl, indazolyl, benzoxazolyl, benzoisoxazolyl, benzothiazolyl, benzoisothiazolyl, benzimidazolyl, quinolyl, pteridinyl, pyrazolopyridinyl, pyrazolopyrimidinyl, imidazolothiazolyl, quinoxazinyl, and indolizinyl. In some embodiments is a method wherein $R_2$ is pyridyl. In some embodiments is a method wherein $R_2$ is heteroaryl substituted with at least one $R_3$ selected from Cl, Br, F, I, $CF_3$, $C_1$-$C_6$alkyl, or $OC_1$-$C_6$alkyl. In some embodiments is a method wherein $R_2$ is heteroaryl substituted with at least one $R_3$ selected from Cl, Br, F, and I. In some embodiments is a method wherein $R_2$ is heteroaryl substituted with at least one F. In some embodiments is a method wherein $L_2$ is —NH—C(=O)—.

In another aspect, described herein is a method for treating stroke or traumatic brain injury in an individual in need thereof comprising administering to the individual a therapeutically effective amount of a compound having the structure of Formula (III):

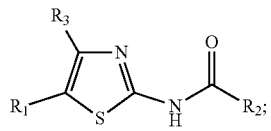

Formula (III)

wherein:
$R_1$ is

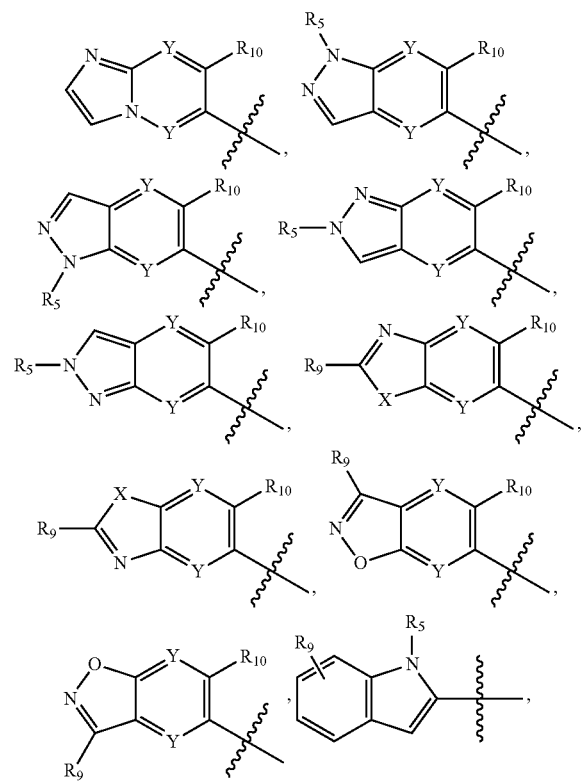

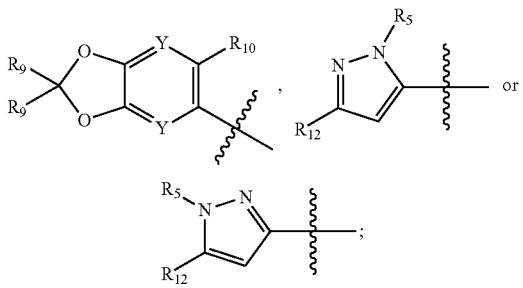

X is S, O, or $NR_5$;

Y is independently selected from $CR_{10}$ or N;

$R_2$ is aryl, heteroaryl, fused aryl or fused heteroaryl; wherein aryl, heteroaryl, fused aryl or fused heteroaryl is optionally substituted with at least one $R_3$;

$R_3$ is independently selected from H, F, D, Cl, Br, I, —CN, —$NO_2$, —OH, —$CF_3$, —$OCF_3$, —$OR_5$, optionally substituted $C_1$-$C_6$alkyl, optionally substituted $C_3$-$C_8$cycloalkyl, optionally substituted $C_1$-$C_6$heteroalkyl, $C_1$-$C_6$haloalkyl, optionally substituted $C_2$-$C_8$heterocycloalkyl, optionally substituted aryl, optionally substituted O-aryl, and optionally substituted heteroaryl;

$R_5$ is selected from H, $C_1$-$C_6$alkyl, $C_1$-$C_6$haloalkyl, $C_3$-$C_8$cycloalkyl, phenyl, and benzyl;

$R_9$ and $R_{10}$ are each independently selected from H, D, optionally substituted $C_1$-$C_6$alkyl, halogen, $C_1$-$C_6$ alkylcarbonyl, or $CF_3$;

$R_{12}$ is selected from CN, —$OR_5$, optionally substituted $C_1$-$C_6$alkyl, $C_1$-$C_6$haloalkyl, and optionally substituted $C_3$-$C_8$cycloalkyl, optionally substituted aryl, optionally substituted O-aryl, and optionally substituted heteroaryl;

or a pharmaceutically acceptable salt, or pharmaceutically acceptable solvate thereof.

In some embodiments is a method wherein $R_2$ is phenyl optionally substituted with at least one $R_3$. In some embodiments is a method wherein $R_2$ is phenyl substituted with at least one $R_3$. In some embodiments is a method wherein $R_2$ is phenyl substituted with at least one $R_3$ selected from F, Cl, Br, and I. In some embodiments is a method wherein $R_2$ is phenyl substituted with at least one $R_3$ selected from Cl, Br, F, I, $CF_3$, $C_1$-$C_6$alkyl, or $OC_1$-$C_6$alkyl. In some embodiments is a method wherein $R_2$ is phenyl substituted with at least one $R_3$ selected from Cl, F, and $CH_3$. In some embodiments is a method wherein $R_2$ is phenyl substituted with at least one F. In some embodiments is a method wherein $R_1$ is

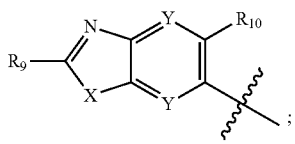

and Y is CH. In some embodiments is a method wherein $R_9$ is optionally substituted $C_1$-$C_6$alkyl. In some embodiments is a method wherein $R_1$ is

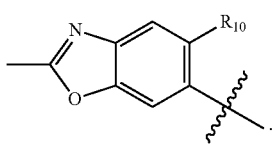

In some embodiments is a method wherein $R_{10}$ is halogen or $C_1$-$C_6$alkyl. In some embodiments is a method wherein $R_{10}$ is Cl. In some embodiments is a method wherein $R_{10}$ is —$CH_3$. In some embodiments is a method wherein $R_{10}$ is —$CH_2CH_3$. In some embodiments is a method wherein $R_2$ is phenyl substituted with two $R_3$, wherein one $R_3$ is F and one $R_3$ is $CH_3$. In some embodiments is a method wherein $R_2$ is phenyl substituted with two $R_3$, wherein one $R_3$ is F and one $R_3$ is Cl. In some embodiments is a method wherein $R_2$ is phenyl substituted with two $R_3$, wherein each $R_3$ is F. In some embodiments is a method wherein $R_2$ is phenyl substituted with three $R_3$, wherein each $R_3$ is F. In some embodiments is a method wherein $R_2$ is heteroaryl substituted with at least one $R_3$. In some embodiments is a method wherein $R_2$ is heteroaryl selected from pyridyl, pyrimidyl, pyridazinyl, pyrazinyl, thienyl, furyl, pyranyl, thiadiazolyl, pyrazolyl, imidazolyl, thiazolyl, isothiazolyl, oxazolyl, isoxazolyl, indolyl, indazolyl, benzoxazolyl, benzoisoxazolyl, benzothiazolyl, benzoisothiazolyl, benzimidazolyl, quinolyl, pteridinyl, pyrazolopyridinyl, pyrazolopyrimidinyl, imidazolothiazolyl, quinoxazinyl, and indolizinyl. In some embodiments is a method wherein $R_2$ is pyridyl. In some embodiments is a method wherein $R_2$ is heteroaryl substituted with at least one $R_3$ selected from Cl, Br, F, I, $CF_3$, $C_1$-$C_6$alkyl, or $OC_1$-$C_6$alkyl. In some embodiments is a method wherein $R_2$ is heteroaryl substituted with at least one $R_3$ selected from Cl, Br, F, and I. In some embodiments is a method wherein $R_2$ is heteroaryl substituted with at least one F.

In another aspect is a method of treating stroke or traumatic brain injury comprising administering to the mammal a compound having the structure of Formula (I), (II), or (III) or pharmaceutically acceptable salt, pharmaceutically acceptable solvate, or pharmaceutically acceptable prodrug thereof, or a pharmaceutical composition comprising same with a pharmaceutically acceptable diluent, excipient or binder.

In another aspect is a method of modulating calcium release activated calcium channel (CRAC) activity in a mammal comprising administering to the mammal a compound of Formula (I), (II), or (III), wherein the compound of Formula (I), (II), or (III) modulates CRAC activity in the mammal.

In a further aspect is a method of treating a disease, disorder or condition in a mammal that would benefit from inhibition of store operated calcium channel activity comprising administering to the mammal a compound of Formula (I), (II), or (III).

In one aspect is a method for treating stroke in an individual comprising administering to the individual a therapeutically effective amount of a compound of Formula (I), (II), or (III) or pharmaceutically acceptable salt or solvate thereof.

In another embodiment is a method for treating traumatic brain injury in an individual comprising administering to the individual a therapeutically effective amount of a compound of Formula (I), (II), or (III) or pharmaceutically acceptable salt or solvate thereof.

In another embodiment is a method for providing neuroprotection to an individual comprising administering to the individual a therapeutically effective amount of a compound of Formula (I), (II), or (III) or pharmaceutically acceptable salt or solvate thereof.

Compounds provided herein are used for modulating intracellular calcium. In one aspect, compounds provided herein modulate SOC channel activity. In one aspect, compounds provided herein modulate CRAC channel activity. In another aspect, compounds provided herein modulate STIM protein activity. In another aspect, compounds provided herein modulate Orai protein activity. In another aspect, compounds provided herein modulate the functional interactions of STIM proteins with Orai proteins. In another aspect, compounds provided herein reduce the number of functional SOC channels. In another aspect, compounds provided herein reduce the number of functional CRAC channels. In one aspect, compounds described herein are SOC channel blockers. In one aspect, compounds described herein are CRAC channel blockers or CRAC channel modulators.

In one aspect, compounds of Formula (I), (II), or (III) are selective inhibitors of CRAC channel activity.

Other objects, features and advantages of the compounds, compositions, methods, and uses described herein will become apparent from the following detailed description. It should be understood, however, that the detailed description and the specific examples, while indicating specific embodiments, are given by way of illustration only, since various changes and modifications within the spirit and scope of the disclosure will become apparent from this detailed description.

DETAILED DESCRIPTION

Figure 1:
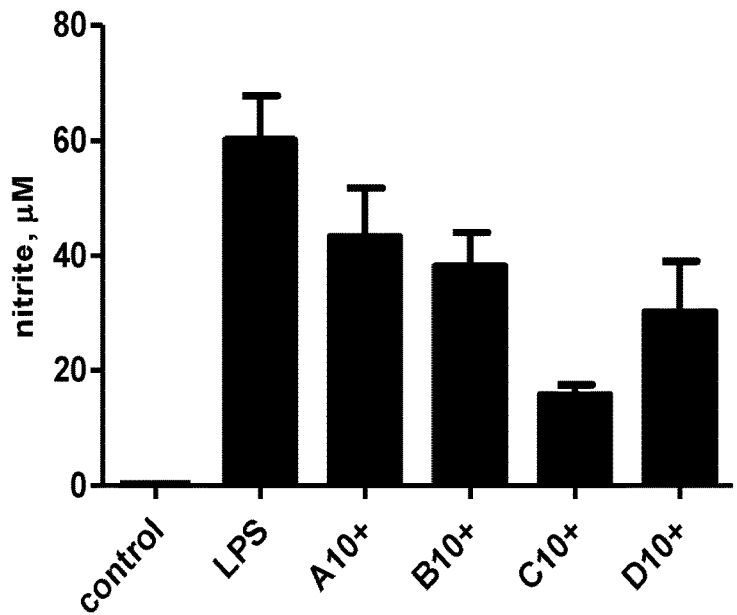
FIG. 1 depicts BV2 cells stimulated with LPS using Griess reagent to estimate NO accumulation for 4 different CRAC inhibitors (Compounds A, B, C, and D) tested at a concentration of 10 uM. Compound A: N-(5-(6-chloro-2,2-difluorobenzo[d][1,3]dioxol-5-yl)pyridin-2-yl)-2,6-difluorobenzamide; Compound B: N-(5-(6-chloro-2,2-difluorobenzo[d][1,3]dioxol-5-yl)pyrazin-2-yl)-2-fluoro-6-methylbenzamide; Compound C: 2,3,6-trifluoro-N-(3-fluoro-4-(1-methyl-3-(trifluoromethyl)-1H-pyrazol-5-yl)phenyl)benzamide; and Compound D: N-(5-(2,5-dimethylbenzo[d]oxazol-6-yl)thiazol-2-yl)-2,3,6-trifluorobenzamide.
Figure 2:
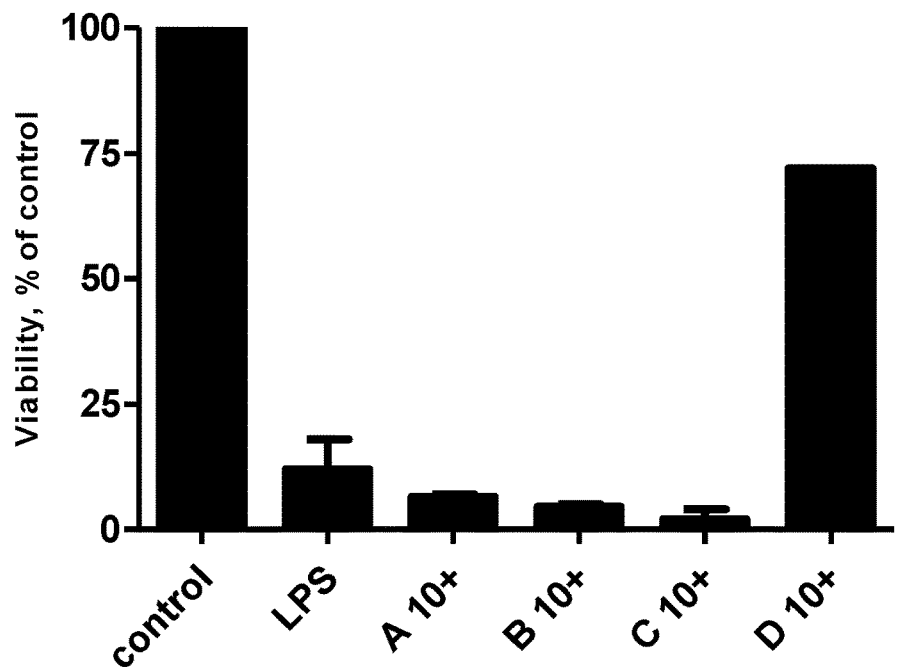
FIG. 2 depicts BV2 cells stimulated with LPS using the MTT assay to assess cell viability for 4 different CRAC inhibitors (Compounds A, B, C, and D) at 10 uM.
Figure 3:
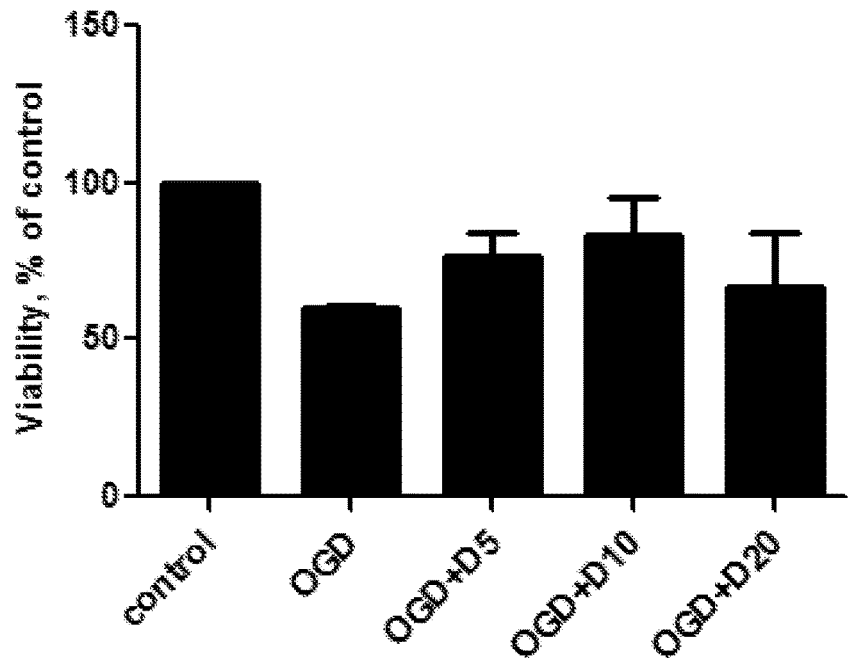
FIG. 3 depicts Neuro2a cells alone exposed to oxygen glucose deprivation (OGD) using the MTT assay to assess cell viability for Compound D at 3 different concentrations.
Figure 4:
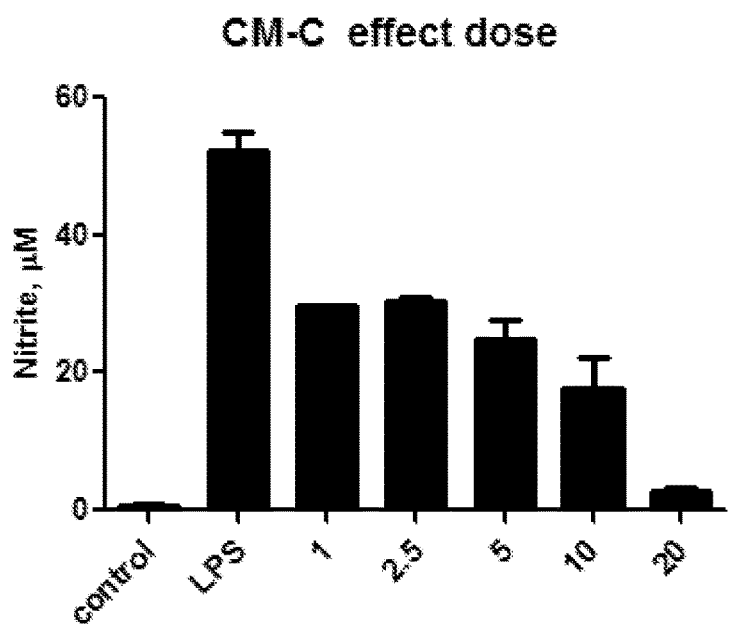
FIG. 4 depicts BV2 cells stimulated with LPS using Griess reagent to estimate NO accumulation for Compound C at 5 different concentrations.
Figure 5:
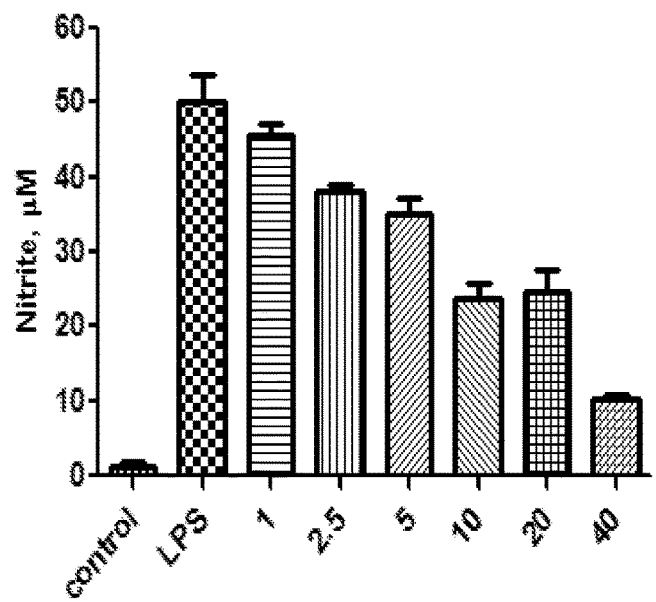
FIG. 5 depicts BV2 cells stimulated with LPS using Griess reagent to estimate NO accumulation for Compound D at 5 different concentrations.
Figure 6:
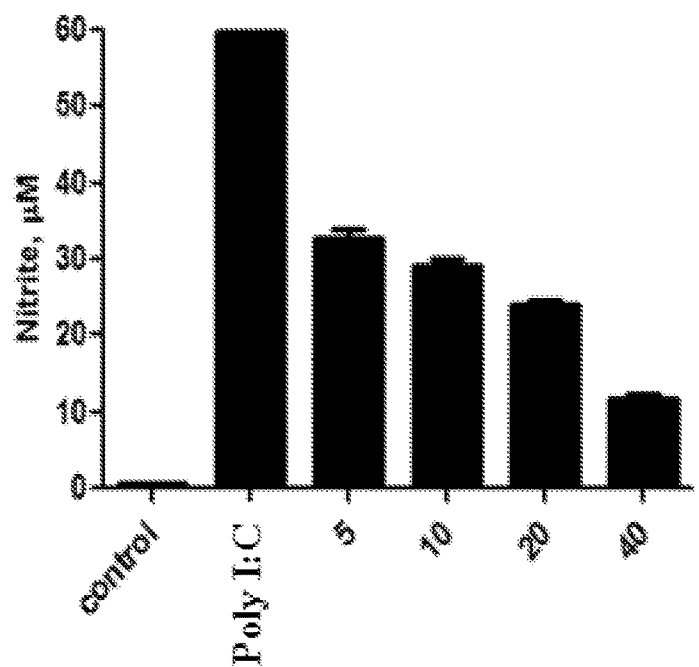
FIG. 6 depicts BV2 cells stimulated with toll-like receptor 3 agonist polyinosinic:polycytidylic acid (poly I:C) using Griess reagent to estimate NO accumulation for Compound D at 4 different concentrations.
Figure 7:
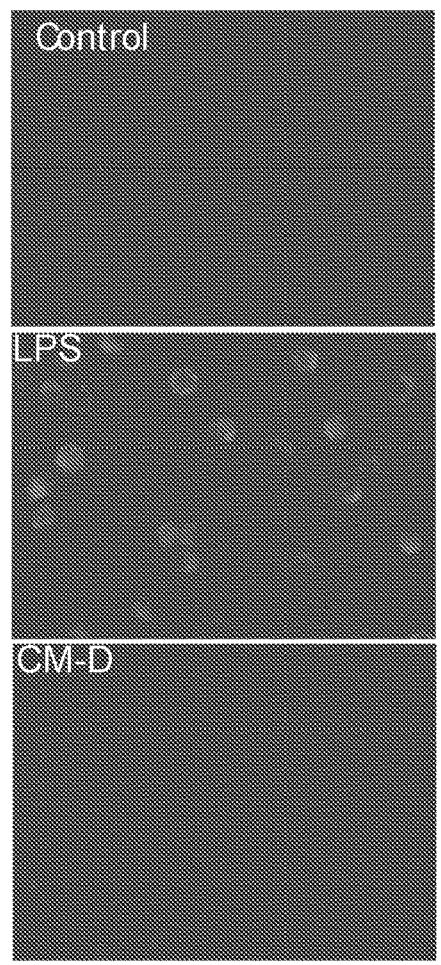
FIG. 7 shows that Compound D at 10 uM blunts LPS activated calcium accumulation in BV2 cells.
Figure 8:
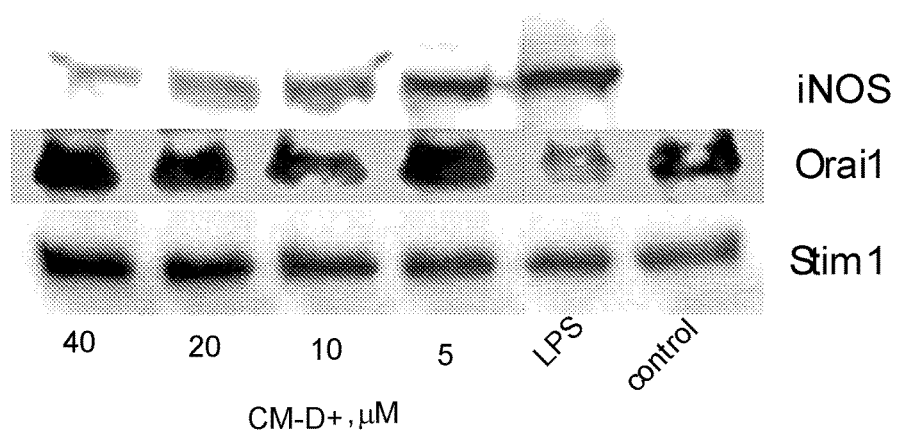
FIG. 8 depicts dose effect of Compound D at 4 different concentrations on expression of CRAC proteins (Stim1 and Oroa1) and iNOS in BV2 cells.

Inflammatory responses following ischemia are known to worsen neurological outcome, and represent a potential target for therapeutic intervention. Recent work has focused on store-operated Ca2+ entry (SOCE) mediated by Ca2+ release-activated (CRAC) channels, and CRAC channels contribute to calcium signaling in immune cells. CRAC channels consist of the Ca2+-binding protein stromal interaction molecule 1 (STIM1) and the calcium modulator channel ORAI1. When Ca2+ stores in the endoplasmic reticulum (ER) have been depleted, STIM1 oligomerizes and translocates to ER-plasma membrane junctions to cluster and activate ORAI1 to elicit Ca2+ influx. Prolonged Ca2+ entry through CRAC channels is crucial in activating the Ca (2+)-sensitive transcription factor of activated cells (NFAT), which is responsible for directing T cell proliferation and cytokine gene expression. Cerebral inflammation can exacerbate injury during ischemia and stroke. Microglia mediate inflammation in the injured brain, but little is known whether CRAC channels are involved.

Described herein, in some embodiments CRAC channel inhibitors are neuroprotectants in brain ischemia and related conditions. A neuron cell line (Neuro-2A, N-2A) was either cultured alone or in co-culture with microglial BV2 cells. Cells were exposed to a cycle of 2 h oxygen glucose deprivation (OGD) plus 22 h reoxygenation in the absence or presence of inhibitor (concentrations 1-50 µM). Cell viability was determined using quantitative calorimetric MTT assay and live/dead assay using immunofluorescence imaging. Toll-like receptor (TLR)-3 and -4 agonists induced inflammatory responses in microglia leading to increased nitric oxide (NO) generation as determined by the Greiss reagent. Intracellular calcium was determined by live fluorescence microscopy using a calcium fluorescent probe. Peroxide levels were measured as an indicator of oxidative stress. CRAC channels proteins (STIM1 & ORAI1), phosphoactive stress kinase JNK1/2, iNOS and expression was determined by immunoblotting assays. NFκB, NFAT and CREB transcription factors activation was measured by phosphorylation and nuclear translocation. Western blots revealed the presence of the canonical CRAC channel proteins STIM1 and ORAI1 in brain derived microglia BV2 cells. CRAC inhibition dose dependently decreased NO release and inflammatory proteins iNOS and COX-2 expression in activated microglia, but did not affect STIM1 or ORAI1 expression. The functional activity of the CRAC channels was evaluated by the effect on intracellular calcium accumulation in BV2 cells. Basal cytoplasmic levels of calcium were elevated by both TLR-3 and -4 agonists compared to controls, and CRAC channel inhibition abrogated this increase. TLR-4 agonist induced JNK1/2 kinase and nuclear factor CREB activation, and these were also attenuated by inhibitor treatment, while NF-κB and NFAT were not (n=1, need to repeat to confirm). OGD significantly decreased N2A neuronal cell viability, which was further exacerbated by BV2 cells. OGD-induced neurotoxic changes in mono and co-cultures were inhibited by the CRAC channel inhibitor (n=3-5, *p<0.05). We show that CRAC channel inhibition confers a neuroprotective effect through decrease of oxidative stress and exerts potent blockade of microglia mediated calcium influx, and inflammatory protein gene expression mediated at least in part through JNK and transcription factor CREB signaling pathways. We suggest a novel anti-inflammatory approach for treating ischemic stroke. Our observations also shed light on new calcium signaling pathways, not previously described in brain ischemia models.

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endoplasmic reticulum, sarcoplasmic reticulum, mitochondria and endocytic organelles including endosomes and lysosomes.

Movement of calcium across cellular membranes is carried out by specialized proteins. For example, calcium from the extracellular space can enter the cell through various calcium channels and a sodium/calcium exchanger and is actively extruded from the cell by calcium pumps and sodium/calcium exchangers. Calcium can also be released from internal stores through inositol trisphosphate or ryanodine receptors and can be taken up by these organelles by means of calcium pumps.

Calcium can enter cells by any of several general classes of channels, including but not limited to, voltage-operated calcium (VOC) channels, store-operated calcium (SOC) channels, and sodium/calcium exchangers operating in reverse mode. VOC channels are activated by membrane depolarization and are found in excitable cells like nerve and muscle and are for the most part not found in nonexcitable cells. Under some conditions, $Ca^{2+}$ can enter cells via $Na^+$—$Ca^{2+}$ exchangers operating in reverse mode.

Endocytosis provides another process by which cells can take up calcium from the extracellular medium through endosomes. In addition, some cells, e.g., exocrine cells, can release calcium via exocytosis.

Cytosolic calcium concentration is tightly regulated with resting levels usually estimated at approximately 0.1 µM in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leak pathways in both the endoplasmic reticulum and plasma membrane. Disturbance of resting cytosolic calcium levels can affect transmission of calcium-dependent signals and give rise to defects in a number of cellular processes. For example, cell proliferation involves a prolonged calcium signaling sequence. Other cellular processes that involve calcium signaling include, but are not limited to, secretion, transcription factor signaling, and fertilization.

Cell-surface receptors that activate phospholipase C (PLC) create cytosolic $Ca^{2+}$ signals from intra- and extracellular sources. An initial transient rise of $[Ca^{2+}]_i$ (intracellular calcium concentration) results from the release of $Ca^{2+}$ from the endoplasmic reticulum (ER), which is triggered by the PLC product, inositol-1,4,5-trisphosphate ($IP_3$), opening $IP_3$ receptors in the ER (Streb et al. Nature, 306, 67-69, 1983). A subsequent phase of sustained $Ca^{2+}$ entry across the plasma membrane then ensues, through specialized store operated calcium (SOC) channels (in the case of immune cells the SOC channels are calcium release-activated calcium (CRAC) channels) in the plasma membrane. Store-operated $Ca^{2+}$ entry (SOCE) is the process in which the emptying of $Ca^{2+}$ stores itself activates $Ca^{2+}$ channels in the plasma membrane to help refill the stores (Putney, *Cell Calcium*, 7, 1-12, 1986; Parekh et al., *Physiol. Rev.* 757-810; 2005). SOCE does more than simply provide $Ca^{2+}$ for refilling stores, but can itself generate sustained $Ca^{2+}$ signals that control such essential functions as gene expression, cell metabolism and exocytosis (Parekh and Putney, *Physiol. Rev.* 85, 757-810 (2005).

In lymphocytes and mast cells, activation of antigen or Fc receptors, respectively causes the release of $Ca^{2+}$ from intracellular stores, which in turn leads to $Ca^{2+}$ influx through CRAC channels in the plasma membrane. The subsequent rise in intracellular $Ca^{2+}$ activates calcineurin, a phosphatase that regulates the transcription factor NFAT. In resting cells, NFAT is phosphorylated and resides in the cytoplasm, but when dephosphorylated by calcineurin, NFAT translocates to the nucleus and activates different genetic programmes depending on stimulation conditions and cell type. In response to infections and during transplant rejection, NFAT partners with the transcription factor AP-1 (Fos-Jun) in the nucleus of "effector" T cells, thereby transactivating cytokine genes, genes that regulate T cell proliferation and other genes that orchestrate an active immune response (Rao et al., *Annu Rev Immunol.*, 1997; 15:707-47). In contrast, in T cells recognizing self antigens, NFAT is activated in the absence of AP-1, and activates a transcriptional programme known as "anergy" that suppresses autoimmune responses (Macian et al., Transcriptional mechanisms underlying lymphocyte tolerance. Cell. 2002 Jun. 14; 109(6):719-31). In a subclass of T cells known as regulatory T cells which suppress autoimmunity mediated by self-reactive effector T cells, NFAT partners with the transcription factor FOXP3 to activate genes responsible for suppressor function (Wu et al., *Cell*, 2006 Jul. 28; 126(2): 375-87; Rudensky A Y, Gavin M, Zheng Y. *Cell.* 2006 Jul. 28; 126(2):253-256).

The endoplasmic reticulum (ER) carries out a variety processes. The ER has a role as both a $Ca^{2+}$ sink and an agonist-sensitive $Ca^{2+}$ store and, protein folding/processing takes place within its lumen. In the latter case, numerous $Ca^{2+}$-dependent chaperone proteins ensure that newly synthesized proteins are folded correctly and sent off to their appropriate destination. The ER is also involved in vesicle trafficking, release of stress signals, regulation of cholesterol metabolism, and apoptosis. Many of these processes require intraluminal $Ca^{2+}$, and protein misfolding, ER stress responses, and apoptosis can all be induced by depleting the ER of $Ca^{2+}$ for prolonged periods of time. Because it contains a finite amount of $Ca^{2+}$, it is clear that ER $Ca^{2+}$ content must fall after release of that $Ca^{2+}$ during stimulation. However, to preserve the functional integrity of the ER, it is vital that the $Ca^{2+}$ content does not fall too low or is maintained at least at a low level. Replenishment of the ER with $Ca^{2+}$ is therefore a central process to all eukaryotic cells. Because a fall in ER $Ca^{2+}$ content activates store-operated $Ca^{2+}$ channels in the plasma membrane, a major function of this $Ca^{2+}$ entry pathway is believed to be maintenance of ER $Ca^{2+}$ levels that are necessary for proper protein synthesis and folding. However, store-operated $Ca^{2+}$ channels have other important roles.

The understanding of store operated calcium entry was provided by electrophysiological studies which established that the process of emptying the stores activated a $Ca^{2+}$ current in mast cells called $Ca^{2+}$ release-activated $Ca^{2+}$ current or $I_{CRAC}$. $I_{CRAC}$ is non-voltage activated, inwardly rectifying, and remarkably selective for $Ca^{2+}$. It is found in several cell types mainly of hemopoietic origin. $I_{CRAC}$ is not the only store-operated current, and it is now apparent that store-operated influx encompasses a family of $Ca^{2+}$-permeable channels, with different properties in different cell types. $I_{CRAC}$ was the first store-operated $Ca^{2+}$ current to be described and remains a popular model for studying store-operated influx.

Store-operated calcium channels can be activated by any procedure that empties ER $Ca^{2+}$ stores; it does not seem to matter how the stores are emptied, the net effect is activation of store-operated $Ca^{2+}$ entry. Physiologically, store emptying is evoked by an increase in the levels of $IP_3$ or other $Ca^{2+}$-releasing signals followed by $Ca^{2+}$ release from the stores. But there are several other methods for emptying stores. These methods include the following:

1) elevation of $IP_3$ in the cytosol (following receptor stimulation or, dialyzing the cytosol with $IP_3$ itself or related congeners like the nonmetabolizable analog $Ins(2,4,5)P_3$);
2) application of a $Ca^{2+}$ ionophore (e.g., ionomycin) to permeabilize the ER membrane;
3) dialyzing the cytoplasm with high concentrations of $Ca^{2+}$ chelators (e.g., EGTA or BAPTA), which chelate $Ca^{2+}$ that leaks from the stores and hence prevent store refilling;
4) exposure to the sarcoplasmic/endoplasmic reticulum $Ca^{2+}$-ATPase (SERCA) inhibitors like thapsigargin, cyclopiazonic acid, and di-tert-butylhydroquinone;
5) sensitizing the $IP_3$ receptors to resting levels of $InsP_3$ with agents like thimerosal; and
6) loading membrane-permeable metal $Ca^{2+}$ chelators like N,N,N',N'-tetrakis(2-pyridylmethyl)ethylene diamine (TPEN) directly into the stores.

Through mass action, TPEN lowers free intraluminal Ca2+ concentration without changing total store $Ca^{2+}$ such that the store depletion-dependent signal is generated.

These methods of emptying stores are not devoid of potential problems. The key feature of store-operated $Ca^{2+}$ entry is that it is the fall in $Ca^{2+}$ content within the stores and not the subsequent rise in cytoplasmic $Ca^{2+}$ concentration that activates the channels. However, ionomycin and SERCA pump blockers generally cause a rise in cytoplasmic $Ca^{2+}$ concentration as a consequence of store depletion, and such a rise in $Ca^{2+}$ could open $Ca^{2+}$-activated cation channels permeable to $Ca^{2+}$. One way to avoid such problems is to use agents under conditions where cytoplasmic $Ca^{2+}$ has been strongly buffered with high concentrations of $Ca^{2+}$ chelator such as EGTA or BAPTA.

Store-Operated Calcium Entry

Reduced calcium concentration in intracellular calcium stores such as the endoplasmic reticulum resulting from release of calcium there from provides a signal for influx of calcium from the extracellular medium into the cell. This influx of calcium, which produces a sustained "plateau" elevation of cytosolic calcium concentration, generally does not rely on voltage-gated plasma membrane channels and does not involve activation of calcium channels by calcium. This calcium influx mechanism is referred to as capacitative calcium entry (CCE), calcium release-activated, store-operated or depletion-operated calcium entry. Store-operated calcium entry can be recorded as an ionic current with distinctive properties. This current is referred to as $I_{SOC}$ (store-operated current) or $I_{CRAC}$ (calcium release-activated current).

Electrophysiological analysis of store-operated or calcium release-activated currents reveal distinct biophysical properties (see, e.g., Parekh and Penner (1997) *Physiol. Rev.*

77:901-930) of these currents. For example, the current can be activated by depletion of intracellular calcium stores (e.g., by non-physiological activators such as thapsigargin, CPA, ionomycin and BAPTA, and physiological activators such as $IP_3$) and can be selective for divalent cations, such as calcium, over monovalent ions in physiological solutions or conditions, can be influenced by changes in cytosolic calcium levels, and can show altered selectivity and conductivity in the presence of low extracellular concentrations of divalent cations. The current may also be blocked or enhanced by 2-APB (depending on concentration) and blocked by SKF96365 and $Gd^{3+}$ and generally can be described as a calcium current that is not strictly voltage-gated.

Patch-clamp studies in mast cells and Jurkat leukemic T cells have established the CRAC entry mechanism as an ion channel with distinctive biophysical characteristics, including a high selectivity for $Ca^{2+}$ paired with an exceedingly low conductance. Furthermore, the CRAC channel was shown to fulfill the rigorous criteria for being store-operated, which is the activation solely by the reduction of $Ca^{2+}$ in the ER rather than by cytosolic $Ca^{2+}$ or other messengers generated by PLC (Prakriya et al., In *Molecular and Cellular Insights into Ion Channel Biology* (ed. Robert Maue) 121-140 (Elsevier Science, Amsterdam, 2004)).

Regulation of Store-Operated Calcium Entry by Intracellular Calcium Stores

Store-operated calcium entry is regulated by the level of calcium within an intracellular calcium store. Intracellular calcium stores can be characterized by sensitivity to agents, which can be physiological or pharmacological, which activate release of calcium from the stores or inhibit uptake of calcium into the stores. Different cells have been studied in characterization of intracellular calcium stores, and stores have been characterized as sensitive to various agents, including, but not limited to, $IP_3$ and compounds that effect the $IP_3$ receptor, thapsigargin, ionomycin and/or cyclic ADP-ribose (cADPR) (see, e.g., Berridge (1993) *Nature* 361:315-325; Churchill and Louis (1999) *Am. J. Physiol.* 276:C426-C434; Dargie et al. (1990) *Cell Regul.* 1:279-290; Gerasimenko et al. (1996) *Cell* 84:473-480; Gromoda et al. (1995) *FEBS Lett.* 360:303-306; Guse et al. (1999) *Nature* 398:70-73).

Accumulation of calcium within endoplasmic reticulum and sarcoplasmic reticulum (SR; a specialized version of the endoplasmic reticulum in striated muscle) storage organelles is achieved through sarcoplasmic-endoplasmic reticulum calcium ATPases (SERCAs), commonly referred to as calcium pumps. During signaling (i.e., when endoplasmic reticulum channels are activated to provide for calcium release from the endoplasmic reticulum into the cytoplasm), endoplasmic reticulum calcium is replenished by the SERCA pump with cytoplasmic calcium that has entered the cell from the extracellular medium (Yu and Hinkle (2000) *J. Biol. Chem.* 275:23648-23653; Hofer et al. (1998) *EMBO J.* 17:1986-1995).

Calcium release channels associated with $IP_3$ and ryanodine receptors provide for controlled release of calcium from endoplasmic and sarcoplasmic reticulum into the cytoplasm resulting in transient increases in cytoplasmic calcium concentration. $IP_3$ receptor-mediated calcium release is triggered by $IP_3$ formed by the break down of plasma membrane phosphoinositides through the action of phospholipase C, which is activated by binding of an agonist to a plasma membrane G protein-coupled receptor or tyrosine kinase. Ryanodine receptor-mediated calcium release is triggered by an increase in cytoplasmic calcium and is referred to as calcium-induced calcium release (CICR). The activity of ryanodine receptors (which have affinity for ryanodine and caffeine) may also be regulated by cyclic ADP-ribose.

Thus, the calcium levels in the stores, and in the cytoplasm, fluctuate. For example, ER free calcium concentration can decrease from a range of about 60-400 μM to about 1-50 μM when HeLa cells are treated with histamine, an agonist of PLC-linked histamine receptors (Miyawaki et al. (1997) *Nature* 388:882-887). Store-operated calcium entry is activated as the free calcium concentration of the intracellular stores is reduced. Depletion of store calcium, as well as a concomitant increase in cytosolic calcium concentration, can thus regulate store-operated calcium entry into cells.

Cytoplasmic Calcium Buffering

Agonist activation of signaling processes in cells can involve dramatic increases in the calcium permeability of the endoplasmic reticulum, for example, through opening of $IP_3$ receptor channels, and the plasma membrane through store-operated calcium entry. These increases in calcium permeability are associated with an increase in cytosolic calcium concentration that can be separated into two components: a "spike" of calcium release from the endoplasmic reticulum during activation of the $IP_3$ receptor and a plateau phase which is a sustained elevation of calcium levels resulting from entry of calcium into the cytoplasm from the extracellular medium. Upon stimulation, the resting intracellular free calcium concentration of about 100 nM can rise globally to greater than 1 μM and higher in microdomains of the cell. The cell modulates these calcium signals with endogenous calcium buffers, including physiological buffering by organelles such as mitochondria, endoplasmic reticulum and Golgi. Mitochondrial uptake of calcium through a uniporter in the inner membrane is driven by the large negative mitochondrial membrane potential, and the accumulated calcium is released slowly through sodium-dependent and -independent exchangers, and, under some circumstances, the permeability transition pore (PTP). Thus, mitochondria can act as calcium buffers by taking up calcium during periods of cellular activation and can slowly release it later. Uptake of calcium into the endoplasmic reticulum is regulated by the sarcoplasmic and endoplasmic reticulum calcium ATPase (SERCA). Uptake of calcium into the Golgi is mediated by a P-type calcium transport ATPase (PMR1/ATP2C1). Additionally, there is evidence that a significant amount of the calcium released upon $IP_3$ receptor activation is extruded from the cell through the action of the plasma membrane calcium ATPase. For example, plasma membrane calcium ATPases provide the dominant mechanism for calcium clearance in human T cells and Jurkat cells, although sodium/calcium exchange also contributes to calcium clearance in human T cells. Within calcium-storing organelles, calcium ions can be bound to specialized calcium-buffering proteins, such as, for example, calsequestrins, calreticulins and calnexins. Additionally, there are calcium-buffering proteins in the cytosol that modulate calcium spikes and assist in redistribution of calcium ions. Thus, proteins and other molecules that participate in any of these and other mechanisms through which cytosolic calcium levels can be reduced are proteins that are involved in, participate in and/or provide for cytoplasmic calcium buffering. Thus, cytoplasmic calcium buffering helps regulate cytoplasmic $Ca^{2+}$ levels during periods of sustained calcium influx through SOC channels or bursts of $Ca^{2+}$ release. Large increases in cytoplasmic Ca2+ levels or store refilling deactivate SOCE.

Downstream Calcium Entry-Mediated Events

In addition to intracellular changes in calcium stores, store-operated calcium entry affects a multitude of events that are consequent to or in addition to the store-operated changes. For example $Ca^{2+}$ influx results in the activation of a large number of calmodulin-dependent enzymes including the serine phosphatase calcineurin. Activation of calcineurin by an increase in intracellular calcium results in acute secretory processes such as mast cell degranulation. Activated mast cells release preformed granules containing histamine, heparin, TNFα and enzymes such as β-hexosaminidase. Some cellular events, such as B and T cell proliferation, require sustained calcineurin signaling, which requires a sustained increase in intracellular calcium. A number of transcription factors are regulated by calcineurin, including NFAT (nuclear factor of activated T cells), MEF2 and NFκB. NFAT transcription factors play important roles in many cell types, including immune cells. In immune cells NFAT mediates transcription of a large number of molecules, including cytokines, chemokines and cell surface receptors. Transcriptional elements for NFAT have been found within the promoters of cytokines such as IL-2, IL-3, IL-4, IL-5, IL-8, IL-13, as well as tumor necrosis factor alpha (TNFα), granulocyte colony-stimulating factor (G-CSF), and gamma-interferon (γ-IFN).

The activity of NFAT proteins is regulated by their phosphorylation level, which in turn is regulated by both calcineurin and NFAT kinases. Activation of calcineurin by an increase in intracellular calcium levels results in dephosphorylation of NFAT and entry into the nucleus. Rephosphorylation of NFAT masks the nuclear localization sequence of NFAT and prevents its entry into the nucleus. Because of its strong dependence on calcineurin-mediated dephosphorylation for localization and activity, NFAT is a sensitive indicator of intracellular free calcium levels.

Stromal Interacting Molecule (STIM) Proteins

In an RNAi screen in *Drosophila* S2 cells using thapsigargin-activated $Ca^{2+}$ entry as a marker for store-operated channels one gene gave a substantially reduced $Ca^{2+}$ entry, and that gene coded for the protein stromal interaction molecule (Stim) (Roos, J. et al. *J. Cell Biol.* 169, 435-445, 2005). There are two homologues of Stim in mammalian cells, STIM1 and STIM2, both of which appear to be distributed ubiquitously (Williams et al., *Biochem J.* 2001 Aug. 1; 357(Pt 3):673-85). STIM1 is the ER $Ca^{2+}$ sensor for store-operated $Ca^{2+}$ entry. STIM1 is a 77 kDa type I membrane protein with multiple predicted protein interaction or signaling domains and is located predominantly in the ER, but also to a limited extent in the plasma membrane.

Knockdown of STIM1 by RNAi substantially reduced $I_{CRAC}$ in Jurkat T cells, and store-operated $Ca^{2+}$ entry in HEK293 epithelial cells and SH-SY5Y neuroblastoma cells. However, knockdown of the closely related STIM2 had no effect. These results indicate an essential role of STIM (*Drosophila*) and STIM1 (mammals) in the mechanism of activation of store-operated channels. It is unlikely that STIM1 is the store-operated channel itself. It has no channel-like sequence, and overexpression of the protein only modestly enhances $Ca^{2+}$ entry. STIM1 is located both on the plasma membrane and intracellular membranes like the ER (Manji et al., *Biochim Biophys Acta.* 2000 Aug. 31; 1481 (1):147-55. 2000). The protein sequence suggests that it spans the membrane once, with its $NH_2$ terminus oriented toward the lumen of the ER or the extracellular space. The $NH_2$ terminus contains an EF-hand domain, and functions as the $Ca^{2+}$ sensor in the ER. The protein also contains protein-protein interaction domains, notably coiled-coiled domains in the cytoplasm and a sterile motif (SAM) in the ER (or extracellular space), both near the predicted transmembrane domain. STIM1 can oligomerize and thus the protein in the ER and plasma membrane could interact bridging the two (Roos, J. et al. *J. Cell Biol.* 169, 435-445 (2005)).

Total internal reflection fluorescence (TIRF) and confocal microscopy reveal that STIM1 is distributed throughout the ER when $Ca^{2+}$ stores are full, but redistributes into discrete puncta near the plasma membrane on store depletion. Although the redistribution of STIM1 into junctional ER regions is slow (Liou, J. et al. *Curr. Biol.* 15, 1235-1241 (2005); Zhang, S. L. et al. *Nature* 437, 902-905 (2005)), it does precede the opening of CRAC channels by several seconds (Wu et al., *J. Cell Biol.* 174, 803-813 (2006)) and is therefore rapid enough to be an essential step in the activation of CRAC channels.

It has been suggested that store depletion causes the insertion of STIM1 into the plasma membrane where it may control store operated calcium entry through the CRAC channels (Zhang, S. L. et al. *Nature* 437, 902-905 (2005); Spassova, M. A. et al. *Proc. Natl Acad. Sci. USA* 103, 4040-4045 (2006)).

The critical evidence for STIM1 as the $Ca^{2+}$ sensor for SOCE is that mutation of predicted $Ca^{2+}$-binding residues of the EF hand structural motif, expected to reduce its affinity for $Ca^{2+}$ and hence mimic the store-depleted state, causes STIM1 to redistribute spontaneously into puncta and trigger constitutive $Ca^{2+}$ influx through SOCs even when stores are full (Spassova, M. A. et al. *Proc. Natl Acad. Sci. USA* 103, 4040-4045 (2006); Liou, J. et al. *Curr. Biol.* 15, 1235-1241 (2005)).

Orai Proteins

Orai1 (also known as CRACM1) is a widely expressed, 33 kDa plasma membrane protein with 4 transmembrane domains and a lack of significant sequence homology to other ion channels (Vig, M. et al. *Science* 312, 1220-1223 (2006); Zhang, S. L. et al. *Proc. Natl Acad. Sci. USA* 103, 9357-9362 (2006)).

Studies of T cells from human patients with a severe combined immunodeficiency (SCID) syndrome, in which T cell receptor engagement or store depletion failed to activate $Ca^{2+}$ entry, was shown to be due to a single point mutation in Orai1 (Feske, S. et al. *Nature* 441, 179-185 (2006)).

Other mammalian Orai homologues exist, e.g. Orai2 and Orai3, however their function is not clearly defined. Orai2 and Orai3 can exhibit SOC channel activity when overexpressed with STIM1 in HEK cells (Mercer, J. C. et al. *J. Biol. Chem.* 281, 24979-24990 (2006)).

Evidence that Orai1 contributes to the CRAC channel pore was obtained by Orai1 mutagenesis studies. Selectivity of the CRAC channel for $Ca^{2+}$ ions was shown by mutations at either Glu 106 or Glu 190, which weaken the ability of $Ca^{2+}$ binding in order block permeation of monovalent cations (similar to mechanisms described for voltage-gated $Ca^{2+}$ channels) (Yeromin, A. V. et al. *Nature* 443, 226-229 (2006); Vig, M. et al. *Curr. Biol.* 16, 2073-2079 (2006); Prakriya, M. et al. *Nature* 443, 230-233 (2006)).

Neutralizing the charge on a pair of aspartates in the I-II loop (Asp 110 and Asp 112) reduces block by $Gd^{3+}$ and block of outward current by extracellular $Ca^{2+}$, indicating that these negatively charged sites may promote accumulation of polyvalent cations near the mouth of the pore.

Currents observed through overexpression of Orai1 closely resemble $I_{CRAC}$, and the fact that Orai1 can form multimers (Yeromin, A. V. et al. *Nature* 443, 226-229 (2006); Vig, M. et al. *Curr. Biol.* 16, 2073-2079 (2006); Prakriya, M. et al. *Nature* 443, 230-233 (2006)), makes it likely that the native CRAC channel is either a multimer of Orai1 alone or in combination with the closely related subunits Orai2 and/or Orai3.

Functional Store Operated Calcium Channels

The characterization of SOC channels has been largely obtained by one type of SOC channel, the CRAC channel. CRAC channel activity is triggered by the loss of $Ca^{2+}$ from the ER lumen, which is coupled to the opening of CRAC channels in the plasma membrane through the actions of STIM1 and Orai1. Depletion of $Ca^{2+}$ is sensed by STIM1, causing it to accumulate in junctional ER adjacent to the plasma membrane. In a TIRF-based $Ca^{2+}$-imaging study to map the locations of open CRAC channels, $[Ca^{2+}]_i$ elevations were seen to co-localize with STIM1 puncta, showing directly that CRAC channels open only in extreme proximity to these sites (Luik, et al., *J. Cell Biol.* 174, 815-825 (2006)).

In cells co-expressing both STIM1 and Orai1, store depletion causes Orai1 itself to move from a dispersed distribution to accumulate in the plasma membrane directly opposite STIM1, enabling STIM1 to activate the channel (Luik, et al., *J. Cell Biol.* 174, 815-825 (2006); Xu, P. et al. *Biochem. Biophys. Res. Commun.* 350, 969-976 (2006)). Thus, CRAC channels are formed by apposed clusters of STIM1 in the ER and Orai1 in the plasma membrane. The junctional gap between the ER and plasma membrane where Orai1/STIM 1 clusters from (about 10-25 nm) may be small enough to permit protein-protein interactions between STIM 1 and Orai1. This is supported by the fact that overexpressed STIM1 and Orai1 can be co-immunoprecipitated (Yeromin, A. V. et al. *Nature* 443, 226-229 (2006); Vig, M. et al. *Curr. Biol.* 16, 2073-2079 (2006)).

Thus, STIM1 and Orai1 interact either directly or as members of a multiprotein complex. Support for this was observed when the expression of the cytosolic portion of STIM1 by itself was sufficient to activate CRAC channels in one study (Huang, G. N. et al. *Nature Cell Biol.* 8, 1003-1010 (2006)), and the effects of deleting the ERM/coiled-coil and other C-terminal domains suggest roles in STIM1 clustering and SOC channel activation (Baba, Y. et al. *Proc. Natl Acad. Sci. USA* 103, 16704-16709 (2006)). On the luminal side of STIM1, the isolated EF-SAM region forms dimers and higher-order multimers on removal of $Ca^{2+}$ in vitro, indicating that STIM1 oligomerization may be an early step in store operated calcium activation (Stathopulos, et al., *J. Biol. Chem.* 281, 35855-35862 (2006)).

In some embodiments, compounds of Formula (I), (II), or (III) described herein modulate intracellular calcium, such as, inhibition or reduction of SOCE and/or $I_{CRAC}$. In other embodiments, the modulation by compounds of Formula (I), (II), or (III) result from a variety of effects, such as, but not limited to, binding to a protein, interaction with a protein, or modulation of interactions, activities, levels or any physical, structural or other property of a protein involved in modulating intracellular calcium (e.g. a STIM protein and/or Orai protein).

For example, methods for assessing binding or interaction of a test agent with a protein involved in modulating intracellular calcium include NMR, mass spectroscopy, fluorescence spectroscopy, scintillation proximity assays, surface plasmon resonance assays and others. Examples of methods for assessing modulation of interactions, activities, levels or any physical, structural or other property of a protein involved in modulating intracellular calcium include, but are not limited to, FRET assays to assess effects on protein interactions, NMR, X-ray crystallography and circular dichroism to assess effects on protein interactions and on physical and structural properties of a protein, and activity assays suitable for assessing a particular activity of a protein.

Monitoring or Assessing Effects on Intracellular Calcium

In some embodiments, monitoring or assessing the effect of a compound of Formula (I), (II), or (III) on intracellular calcium in any of the screening/identification methods described herein, a direct or indirect evaluation or measurement of cellular (including cytosolic and intracellular organelle or compartment) calcium and/or movement of ions into, within or out of a cell, organelle, calcium store or portions thereof (e.g., a membrane) are conducted. A variety of methods are described herein for evaluating calcium levels and ion movements or flux. The particular method used and the conditions employed depend on whether a particular aspect of intracellular calcium is being monitored or assessed. For example, in some embodiments described herein, reagents and conditions are known, and are used, for specifically evaluating store-operated calcium entry, resting cytosolic calcium levels, calcium buffering and calcium levels and uptake by or release from intracellular organelles and calcium stores. In other embodiments, the effect of a compound of Formula (I), (II), or (III) on intracellular calcium is monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Methods of Modulating Intracellular Calcium

In some embodiments, modulation of intracellular calcium is any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In some embodiments, intracellular calcium modulation involves alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. In some embodiments, modulation of intracellular calcium involves an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE), in an immune system cell (e.g., a lymphocyte, white blood cell, T cell, B cell), a fibroblast (or a cell derived from a fibroblast), or an epidermal, dermal or skin cell (e.g., a keratinocyte). In some embodiments, the step of modulating one or more proteins involved in modulating intracellular calcium (e.g. a STIM protein and/or Orai protein) involves, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then in other embodiments, modulating involves reducing the level of, expression of, an activity or function of, or a molecular interaction of a protein, e.g. a STIM protein and/or Orai protein.

Compounds

Compounds described herein modulate intracellular calcium and may be used in the treatment of diseases or conditions where modulation of intracellular calcium has a beneficial effect. In one embodiment, compounds described herein inhibit store operated calcium entry. In one embodiment, compounds of Formula (I), (II), or (III) interrupt the assembly of SOCE units. In another embodiment, compounds of Formula (I), (II), or (III) alter the functional interactions of proteins that form store operated calcium channel complexes. In one embodiment, compounds of Formula (I), (II), or (III) alter the functional interactions of STIM1 with Orai1. In other embodiments, compounds of Formula (I), (II), or (III) are SOC channel pore blockers. In other embodiments, compounds of Formula (I), (II), or (III) are CRAC channel pore blockers.

In one aspect, compounds described herein inhibit the electrophysiological current ($I_{SOC}$) directly associated with activated SOC channels. In another aspect, compounds described herein inhibit the electrophysiological current ($I_{CRAC}$) directly associated with activated CRAC channels.

The diseases or disorders that may benefit from modulation of intracellular calcium include, but are not limited to, stroke and traumatic brain injury.

Compounds described herein modulate an activity of, modulate an interaction of, or binds to, or interacts with at least one portion of a protein in the store operated calcium channel complex. In one embodiment, compounds described herein modulate an activity of, modulate an interaction of, or binds to, or interacts with at least one portion of a protein in the calcium release activated calcium channel complex. In one aspect, compounds described herein reduce the level of functional store operated calcium channel complexes. In one aspect, compounds described herein reduce the level of activated store operated calcium channel complexes. In one aspect, store operated calcium channel complexes are calcium release activated calcium channel complexes.

Compounds described herein for treatment of a disease or disorder, when administered to a subject having a disease or disorder effectively reduces, ameliorates or eliminates a symptom or manifestation of the disease or disorder. Compounds described herein can also be administered to a subject predisposed to a disease or disorder who does not yet manifest a symptom of the disease or disorder, prevents or delays development of the symptoms. The agent can have such effects alone or in combination with other agents, or may function to enhance a therapeutic effect of another agent.

Compounds described herein, pharmaceutically acceptable salts, pharmaceutically acceptable prodrugs, or pharmaceutically acceptable solvates thereof, modulate intracellular calcium, and may be used to treat patients where modulation of intracellular calcium provides benefit.

In one aspect, the compounds described herein are selective inhibitors of CRAC channel activity.

In another aspect, described herein is a compound having the structure of Formula (I):

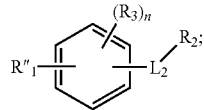

Formula (I)

wherein:

$R''_1$ is

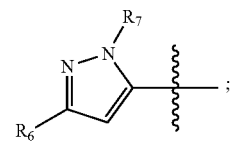

$L_2$ is —NH—C(=O)—, or —C(=O)NH—;

$R_2$ is phenyl or pyridyl; wherein phenyl or pyridyl is optionally substituted with at least one $R_3$;

$R_3$ is independently selected from F, Cl, Br, I, —CN, —NO$_2$, —OH, —OCF$_3$, —OR$_5$, and —N(R$_5$)$_2$;

n is an integer selected from 1-4;

each $R_5$ is independently selected from $C_1$-$C_6$alkyl, and $C_1$-$C_6$haloalkyl;

$R_7$ is $C_1$-$C_6$alkyl; and $R_6$ is selected from F, Cl, Br, I, —CN, —NO$_2$, —OH, —CF$_3$, —OCF$_3$, —OR$_5$, $C_1$-$C_6$alkyl, $C_3$-$C_8$cycloalkyl, and $C_1$-$C_6$haloalkyl;

or a pharmaceutically acceptable salt or pharmaceutically acceptable solvate thereof.

In some embodiments is a method for treating stroke or traumatic brain injury in an individual in need thereof comprising administering to the individual a therapeutically effective amount of a compound having the structure of Formula (IA):

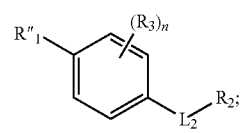

Formula (IA)

In some embodiments is a method wherein $L_2$ is —NH—C(=O)—. In some embodiments is a method wherein $R_2$ is phenyl optionally substituted with at least one $R_3$. In some embodiments is a method wherein $R_2$ is phenyl substituted with at least one $R_3$ selected from F, Cl, Br, I, —CN, —OH, —OCF$_3$, —OR$_5$, and —N(R$_5$)$_2$. In some embodiments is a method wherein $R_6$ is selected from —CF$_3$, —OCF$_3$, —OR$_5$, $C_1$-$C_6$alkyl, and $C_3$-$C_8$cycloalkyl. In some embodiments is a method wherein $R_6$ is —CF$_3$ and $R_7$ is —CH$_3$. In some embodiments is a method wherein $R_6$ is —CF$_3$ and $R_7$ is —CH$_2$CH$_3$. In some embodiments is a method wherein n is 1. In some embodiments is a method wherein $R_3$ is fluorine. In some embodiments is a method wherein $R_2$ is phenyl substituted with at least 2 F substituents. In some embodiments is a method wherein $R_2$ is phenyl substituted with at least 3 F substituents. In some embodiments is a method wherein $R_2$ is pyridyl. In some embodiments is a method wherein $R_2$ is pyridyl substituted with at least one $R_3$ selected from F, Cl, Br, —OH, —CN, —OCF$_3$, —OR$_5$, and —N(R$_5$)$_2$. In some embodiments is a method wherein R$_2$ is pyridyl substituted with at least one fluorine.

In another aspect is a compound having the structure of Formula (II):

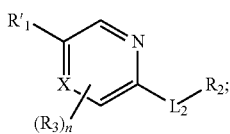

Formula (II)

wherein:
R'$_1$ is

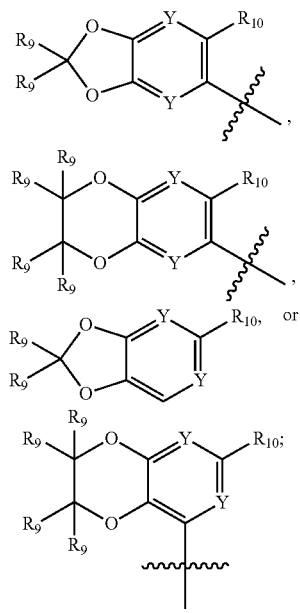

L$_2$ is —NH—C(═O)—, or —C(═O)NH—;
X is CR$_3$ or N;
Y is independently selected from CR$_9$ or N;
R$_2$ is C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, C$_1$-C$_4$alkyleneC$_2$-C$_8$heterocycloalkyl, aryl, heteroaryl, fused aryl or fused heteroaryl; wherein C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, C$_1$-C$_4$alkyleneC$_2$-C$_8$heterocycloalkyl, aryl, heteroaryl, fused aryl or fused heteroaryl is optionally substituted with at least one R$_3$;
R$_3$ is independently selected from H, F, D, Cl, Br, I, —CN, —NO$_2$, —OH, —CF$_3$, —OCF$_3$, —OR$_5$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, optionally substituted O-aryl, optionally substituted heteroaryl,
n is an integer selected from 0-2;
R$_9$ is independently selected from H, D, halogen, C$_1$-C$_6$alkyl, C$_1$-C$_6$haloalkyl, —OR$_5$, —OCF$_3$, C$_1$-C$_6$ carbonylalkyl, or —CF$_3$; or two R$_9$ attached to the same carbon atom form an oxetane ring;
R$_{10}$ is selected from halogen, C$_1$-C$_6$alkyl, C$_1$-C$_6$haloalkyl, —OR$_5$, —OCF$_3$, C$_1$-C$_6$ carbonylalkyl, or —CF$_3$;
R$_5$ is independently selected from H, C$_1$-C$_6$alkyl, C$_1$-C$_6$haloalkyl, C$_3$-C$_8$cycloalkyl, phenyl, and benzyl;

or a pharmaceutically acceptable salt, or pharmaceutically acceptable solvate thereof.

In some embodiments is a method wherein X is CH. In some embodiments is a method wherein X is N. In some embodiments is a method wherein R'$_1$ is

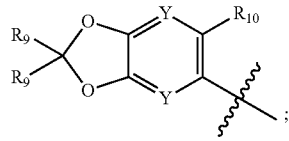

and Y is CH. In some embodiments is a method wherein R$_2$ is phenyl optionally substituted with at least one R$_3$. In some embodiments is a method wherein R$_2$ is phenyl substituted with at least one R$_3$ selected from Cl, Br, F, I, CF$_3$, C$_1$-C$_6$alkyl, or OC$_1$-C$_6$alkyl. In some embodiments is a method wherein R$_2$ is phenyl substituted with at least one R$_3$ selected from Cl, F, and CH$_3$. In some embodiments is a method wherein R$_2$ is phenyl substituted with at least one F. In some embodiments is a method wherein at least one R$_9$ is halogen. In some embodiments is a method wherein R'$_1$ is

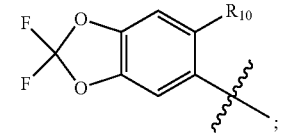

and n is 0. In some embodiments is a method wherein R$_{10}$ is halogen or C$_1$-C$_6$alkyl. In some embodiments is a method wherein R$_{10}$ is Cl. In some embodiments is a method wherein R$_{10}$ is —CH$_3$. In some embodiments is a method wherein R$_{10}$ is —CH$_2$CH$_3$. In some embodiments is a method wherein R$_2$ is phenyl substituted with two R$_3$, wherein one R$_3$ is F and one R$_3$ is CH$_3$. In some embodiments is a method wherein R$_2$ is phenyl substituted with two R$_3$, wherein one R$_3$ is F and one R$_3$ is Cl. In some embodiments is a method wherein R$_2$ is phenyl substituted with two R$_3$, wherein each R$_3$ is F. In some embodiments is a method wherein R$_2$ is phenyl substituted with three R$_3$, wherein each R$_3$ is F. In some embodiments is a method wherein R$_2$ is heteroaryl substituted with at least one R$_3$. In some embodiments is a method wherein R$_2$ is heteroaryl selected from pyridyl, pyrimidyl, pyridazinyl, pyrazinyl, thienyl, furyl, pyranyl, thiadiazolyl, pyrazolyl, imidazolyl, thiazolyl, isothiazolyl, oxazolyl, isoxazolyl, indolyl, indazolyl, benzoxazolyl, benzoisoxazolyl, benzothiazolyl, benzoisothiazolyl, benzimidazolyl, quinolyl, pteridinyl, pyrazolopyridinyl, pyrazolopyrimidinyl, imidazolothiazolyl, quinoxazinyl, and indolizinyl. In some embodiments is a method wherein R$_2$ is pyridyl. In some embodiments is a method wherein R$_2$ is heteroaryl substituted with at least one R$_3$ selected from Cl, Br, F, I, CF$_3$, C$_1$-C$_6$alkyl, or OC$_1$-C$_6$alkyl. In some embodiments is a method wherein R$_2$ is heteroaryl substituted with at least one R$_3$ selected from Cl, Br, F, and I. In some embodiments is a method wherein R$_2$ is heteroaryl substituted with at least one F. In some embodiments is a method wherein L$_2$ is —NH—C(═O)—.

Also disclosed herein is a compound of Formula (III) having the structure:

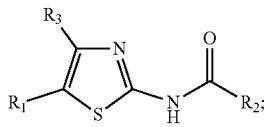

Formula (III)

wherein:

R₁ is

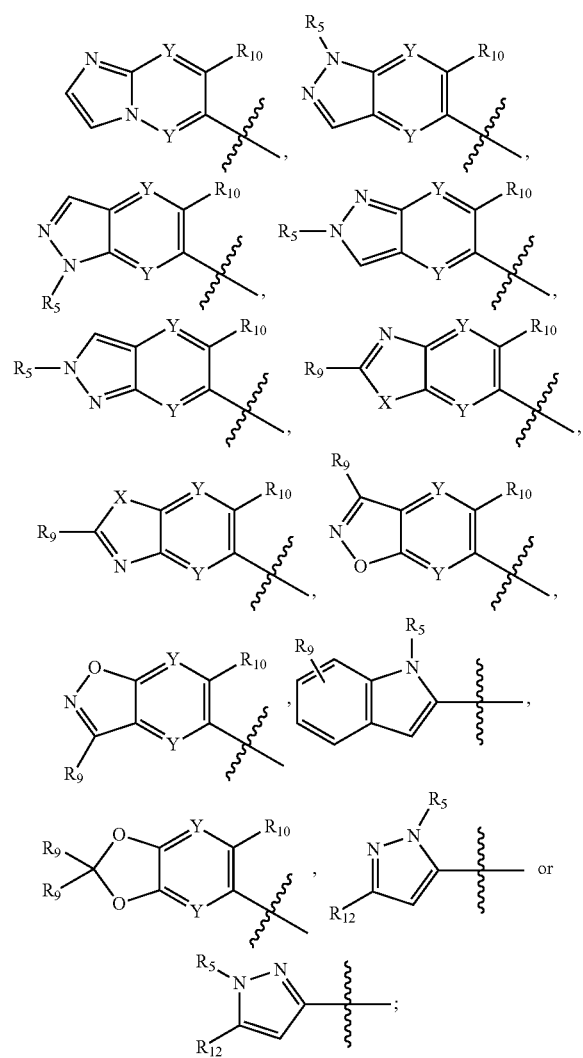

X is S, O, or NR₅;

Y is independently selected from CR₁₀ or N;

R₂ is aryl, heteroaryl, fused aryl or fused heteroaryl; wherein aryl, heteroaryl, fused aryl or fused heteroaryl is optionally substituted with at least one R₃;

R₃ is independently selected from H, F, D, Cl, Br, I, —CN, —NO₂, —OH, —CF₃, —OCF₃, —OR₅, optionally substituted $C_1$-$C_6$alkyl, optionally substituted $C_3$-$C_8$cycloalkyl, optionally substituted $C_1$-$C_6$heteroalkyl, $C_1$-$C_6$haloalkyl, optionally substituted $C_2$-$C_8$heterocycloalkyl, optionally substituted aryl, optionally substituted O-aryl, and optionally substituted heteroaryl;

R₅ is selected from H, $C_1$-$C_6$alkyl, $C_1$-$C_6$haloalkyl, $C_3$-$C_8$cycloalkyl, phenyl, and benzyl;

R₉ and R₁₀ are each independently selected from H, D, optionally substituted $C_1$-$C_6$alkyl, halogen, $C_1$-$C_6$ alkylcarbonyl, or CF₃;

R₁₂ is selected from CN, —OR₅, optionally substituted $C_1$-$C_6$alkyl, $C_1$-$C_6$haloalkyl, and optionally substituted $C_3$-$C_8$cycloalkyl, optionally substituted aryl, optionally substituted O-aryl, and optionally substituted heteroaryl;

or a pharmaceutically acceptable salt, or pharmaceutically acceptable solvate thereof.

In some embodiments is a method wherein R₂ is phenyl optionally substituted with at least one R₃. In some embodiments is a method wherein R₂ is phenyl substituted with at least one R₃. In some embodiments is a method wherein R₂ is phenyl substituted with at least one R₃ selected from F, Cl, Br, and I. In some embodiments is a method wherein R₂ is phenyl substituted with at least one R₃ selected from Cl, Br, F, I, CF₃, $C_1$-$C_6$alkyl, or $OC_1$-$C_6$alkyl. In some embodiments is a method wherein R₂ is phenyl substituted with at least one R₃ selected from Cl, F, and CH₃. In some embodiments is a method wherein R₂ is phenyl substituted with at least one F. In some embodiments is a method wherein R₁ is

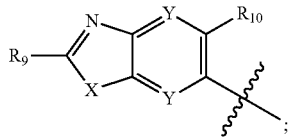

and Y is CH. In some embodiments is a method wherein R₉ is optionally substituted $C_1$-$C_6$alkyl. In some embodiments is a method wherein R₁ is

In some embodiments is a method wherein R₁₀ is halogen or $C_1$-$C_6$alkyl. In some embodiments is a method wherein R₁₀ is Cl. In some embodiments is a method wherein R₁₀ is —CH₃. In some embodiments is a method wherein R₁₀ is —CH₂CH₃. In some embodiments is a method wherein R₂ is phenyl substituted with two R₃, wherein one R₃ is F and one R₃ is CH₃. In some embodiments is a method wherein R₂ is phenyl substituted with two R₃, wherein one R₃ is F and one R₃ is Cl. In some embodiments is a method wherein R₂ is phenyl substituted with two R₃, wherein each R₃ is F. In some embodiments is a method wherein R₂ is phenyl substituted with three R₃, wherein each R₃ is F. In some embodiments is a method wherein R₂ is heteroaryl substituted with at least one R₃. In some embodiments is a method wherein R₂ is heteroaryl selected from pyridyl, pyrimidyl, pyridazinyl, pyrazinyl, thienyl, furyl, pyranyl, thiadiazolyl, pyrazolyl, imidazolyl, thiazolyl, isothiazolyl, oxazolyl, isoxazolyl, indolyl, indazolyl, benzoxazolyl, benzoisoxazolyl, benzothiazolyl, benzoisothiazolyl, benzimidazolyl, quinolyl, pteridinyl, pyrazolopyridinyl, pyrazolopyrimidinyl, imidazolothiazolyl, quinoxazinyl, and indolizinyl. In some embodiments is a method wherein $R_2$ is pyridyl. In some embodiments is a method wherein $R_2$ is heteroaryl substituted with at least one $R_3$ selected from Cl, Br, F, I, $CF_3$, $C_1$-$C_6$alkyl, or $OC_1$-$C_6$alkyl. In some embodiments is a method wherein $R_2$ is heteroaryl substituted with at least one $R_3$ selected from Cl, Br, F, and I. In some embodiments is a method wherein $R_2$ is heteroaryl substituted with at least one F.

In another aspect is a pharmaceutical composition comprising a pharmaceutically acceptable diluent, excipient or binder, and a compound having the structure of Formula (I), (II), or (III) or pharmaceutically acceptable salt, pharmaceutically acceptable prodrug, or pharmaceutically acceptable solvate thereof.

In another aspect is a method of treating a disease, disorder or condition in a mammal that would benefit from inhibition of store operated calcium channel activity comprising administering to the mammal a compound having the structure of Formula (I), (II), or (III) or pharmaceutically acceptable salt, pharmaceutically acceptable solvate, or pharmaceutically acceptable prodrug thereof, or a pharmaceutical composition comprising same with a pharmaceutically acceptable diluent, excipient or binder.

In certain embodiments, the disease, disorder or condition in a mammal is selected from diseases/disorders involving inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, organ transplant rejection, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma, psoriasis, multiple sclerosis, Sjogren's syndrome, and autoimmune diseases or disorders.

In another aspect is a method of modulating store-operated calcium (SOC) channel activity comprising contacting the SOC channel complex, or portion thereof, with a compound of Formula (I), (II), or (III) or pharmaceutically acceptable salt, pharmaceutically acceptable solvate, or pharmaceutically acceptable prodrug thereof, or a pharmaceutical composition comprising same with a pharmaceutically acceptable diluent, excipient or binder.

Also presented herein is a method of modulating calcium release activated calcium channel (CRAC) activity in a mammal comprising administering a compound of Formula (I), (II), or (III) or pharmaceutically acceptable salt, pharmaceutically acceptable solvate, or pharmaceutically acceptable prodrug thereof.

In one embodiment is a method of modulating calcium release activated calcium channel (CRAC) activity in a mammal comprising administering a compound of Formula (I), (II), or (III), or pharmaceutically acceptable salt, pharmaceutically acceptable solvate, or pharmaceutically acceptable prodrug thereof wherein the compound of Formula (I), (II), or (III) modulates an activity of, modulates an interaction of, modulates the level of, or binds to, or interacts with at least one component of the calcium release activated (CRAC) channel complex selected from stromal interaction molecules (STIM) family of proteins.

In another embodiment is a method of modulating calcium release activated calcium channel (CRAC) activity in a mammal comprising administering a compound of Formula (I), (II), or (III), or pharmaceutically acceptable salt, pharmaceutically acceptable solvate, or pharmaceutically acceptable prodrug thereof wherein the compound of Formula (I), (II), or (III) modulates an activity of, modulates an interaction of, or modulates the level of, or binds to, or interacts with STIM1 or STIM2.

In yet another embodiment is a method of modulating calcium release activated calcium channel (CRAC) activity in a mammal comprising administering a compound of Formula (I), (II), or (III), or pharmaceutically acceptable salt, pharmaceutically acceptable solvate, or pharmaceutically acceptable prodrug thereof wherein modulating calcium release activated calcium (CRAC) channel activity with a compound of Formula (I), (II), or (III) inhibits store-operated calcium entry (SOCE).

In a further embodiment is a method of modulating calcium release activated calcium channel (CRAC) activity in a mammal comprising administering a compound of Formula (I), (II), or (III), or pharmaceutically acceptable salt, pharmaceutically acceptable solvate, or pharmaceutically acceptable prodrug thereof wherein modulating calcium release activated calcium (CRAC) channel activity with a compound of Formula (I), (II), or (III) inhibits the electrophysiological current ($I_{CRAC}$) directly associated with activated CRAC channels.

In yet a further embodiment is a method of modulating calcium release activated calcium channel (CRAC) activity in a mammal comprising administering a compound of Formula (I), (II), or (III), or pharmaceutically acceptable salt, pharmaceutically acceptable solvate, or pharmaceutically acceptable prodrug thereof wherein the compound of Formula (I), (II), or (III) inhibits SOCE with an $IC_{50}$ below 10 µM.

In another embodiment is a method of modulating calcium release activated calcium channel (CRAC) activity in a mammal comprising administering a compound of Formula (I), (II), or (III), or pharmaceutically acceptable salt, pharmaceutically acceptable solvate, or pharmaceutically acceptable prodrug thereof wherein the compound of Formula (I), (II), or (III) inhibits electrophysiological current ($I_{CRAC}$) directly associated with activated CRAC channels at a concentration below 10 µM.

In one aspect is a method of treating a disease, disorder or condition in a mammal that would benefit from inhibition of store operated calcium channel activity comprising administering to the mammal a compound of Formula (I), (II), or (III), or pharmaceutically acceptable salt, pharmaceutically acceptable solvate, or pharmaceutically acceptable prodrug thereof.

In one embodiment is a method of treating a disease, disorder or condition in a mammal that would benefit from inhibition of store operated calcium channel activity comprising administering to the mammal a compound of Formula (I), (II), or (III), or pharmaceutically acceptable salt, pharmaceutically acceptable solvate, or pharmaceutically acceptable prodrug thereof wherein the compound of v modulates the activity of, modulates an interaction of, or binds to, or interacts with a mammalian STIM1 protein, or a mammalian STIM2 protein.

In yet another embodiment is a method of treating a disease, disorder or condition in a mammal that would benefit from inhibition of store operated calcium channel activity comprising administering to the mammal a compound of Formula (I), (II), or (III), or pharmaceutically acceptable salt, pharmaceutically acceptable solvate, or pharmaceutically acceptable prodrug thereof wherein the disease, disorder or condition is stroke.

In a further embodiment is a method of treating a disease, disorder or condition in a mammal that would benefit from inhibition of store operated calcium channel activity comprising administering to the mammal a compound of Formula (I), (II), or (III), or pharmaceutically acceptable salt, pharmaceutically acceptable solvate, or pharmaceutically acceptable prodrug thereof wherein the disease, disorder or condition is traumatic brain injury.

In a further embodiment is a method of treating a disease, disorder or condition in a mammal that would benefit from neuroprotection comprising administering to the mammal a compound of Formula (I), (II), or (III), or pharmaceutically acceptable salt, pharmaceutically acceptable solvate, or pharmaceutically acceptable prodrug thereof.

In yet a further embodiment is a method of treating a disease, disorder or condition in a mammal that would benefit from inhibition of store operated calcium channel activity comprising administering to the mammal a compound of Formula (I), (II), or (III), or pharmaceutically acceptable salt, pharmaceutically acceptable solvate, or pharmaceutically acceptable prodrug thereof further comprising administering to the mammal a second therapeutic agent.

In another embodiment is a method of treating a disease, disorder or condition in a mammal that would benefit from inhibition of store operated calcium channel activity comprising administering to the mammal a compound of Formula (I), (II), or (III), or pharmaceutically acceptable salt, pharmaceutically acceptable solvate, or pharmaceutically acceptable prodrug thereof, wherein the second therapeutic agent is selected from immunosuppressant's, glucocorticoids, non-steroidal anti-inflammatory drugs, Cox-2-specific inhibitors, leflunomide, gold thioglucose, gold thiomalate, aurofin, sulfasalazine, hydroxychloroquinine, minocycline, anti-TNF-α agents, abatacept, anakinra, interferon-β, interferon-γ, interleukin-2, allergy vaccines, antihistamines, antileukotrienes, beta-agonists, theophylline, and anticholinergics.

In yet another embodiment is a method of treating a disease, disorder or condition in a mammal that would benefit from inhibition of store operated calcium channel activity comprising administering to the mammal a compound of Formula (I), (II), or (III), or pharmaceutically acceptable salt, pharmaceutically acceptable solvate, or pharmaceutically acceptable prodrug thereof, wherein the second therapeutic agent is selected from tacrolimus, cyclosporin, rapamicin, methotrexate, cyclophosphamide, azathioprine, mercaptopurine, mycophenolate, or FTY720, prednisone, cortisone acetate, prednisolone, methylprednisolone, dexamethasone, betamethasone, triamcinolone, beclometasone, fludrocortisone acetate, deoxycorticosterone acetate, aldosterone, aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502, JTE-522, L-745,337 and NS398, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, allergy vaccines, antihistamines, antileukotrienes, beta-agonists, theophylline, and anticholinergics.

Also described herein is a method of inhibiting store-operated calcium entry (SOCE) activation of nuclear factor of activated T cells (NFAT) in a mammal comprising administering a compound of Formula (I), (II), or (III) or pharmaceutically acceptable salt, pharmaceutically acceptable solvate, or pharmaceutically acceptable prodrug thereof.

In one embodiment is a method of inhibiting store-operated calcium entry (SOCE) activation of nuclear factor of activated T cells (NFAT) in a mammal comprising administering a compound of Formula (I), (II), or (III), or pharmaceutically acceptable salt, pharmaceutically acceptable solvate, or pharmaceutically acceptable prodrug thereof, wherein the compound of Formula (I), (II), or (III) modulates an interaction of, or modulates the level of, or binds to, or interacts with a mammalian STIM1 protein, or a mammalian STIM2 protein.

In another aspect is a method of decreasing cytokine expression by inhibiting the store-operated calcium entry activation of NFAT in a mammal comprising administering a compound of Formula (I), (II), or (III), or pharmaceutically acceptable salt, pharmaceutically acceptable solvate, or pharmaceutically acceptable prodrug thereof.

In another embodiment is a method of decreasing cytokine expression by inhibiting the store-operated calcium entry activation of NFAT in a mammal comprising administering a compound of Formula (I), (II), or (III), or pharmaceutically acceptable salt, pharmaceutically acceptable solvate, or pharmaceutically acceptable prodrug thereof wherein the compound of Formula (I), (II), or (III) modulates an interaction of, or modulates the level of, or binds to, or interacts with a mammalian STIM1 protein or a mammalian STIM2 protein.

In yet another embodiment is a method of decreasing cytokine expression by inhibiting the store-operated calcium entry activation of NFAT in a mammal comprising administering a compound of Formula (I), (II), or (III), or pharmaceutically acceptable salt, pharmaceutically acceptable solvate, or pharmaceutically acceptable prodrug thereof wherein the cytokine is selected from IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, IL-1 RA, granulocyte colony stimulating factor (G-CSF), granulocyte-macrophage colony stimulating factor (GM-CSF), oncostatin M, erythropoietin, leukemia inhibitory factor (LIF), interferons, gamma-interferon (γ-IFN), B7.1 (CD80), B7.2 (B70, CD86), TNF-α, TNF-β, LT-β, CD40 ligand, Fas ligand, CD27 ligand, CD30 ligand, 4-1BBL, Trail, and migration inhibitory factor (MIF).

Further Forms of Compounds

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some situations, compounds may exist as tautomers. All tautomers are included within the formulas described herein.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. In some embodiments, by virtue of knowledge of pharmacodynamic processes and drug metabolism in vivo, once a pharmaceutically active compound is determined, prodrugs of the compound are designed. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem. Vol.* 46, no. 24, 5097-5116, 2003; Aesop Cho, "Recent Advances in Oral Prodrug Discovery", *Annual Reports in Medicinal Chemistry*, Vol. 41, 395-407, 2006).

Prodrug forms of the herein described compounds, wherein the prodrug is metabolized in vivo to produce a compound having the structure of Formula (I), (II), or (III) as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure).

Sites on the aromatic ring portion of compounds described herein can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by other means, including, but not limited to, the use of chromophores or fluorescent moieties, bioluminescent labels, photoactivatable or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^3H$ and $^{14}C$ are incorporated, are useful in drug and/or substrate tissue distribution assays. Further, substitution with isotopes such as deuterium, i.e., $^2H$, can afford certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein, such as compounds of Formula (I), (II), or (III), are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999) (all of which are incorporated by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

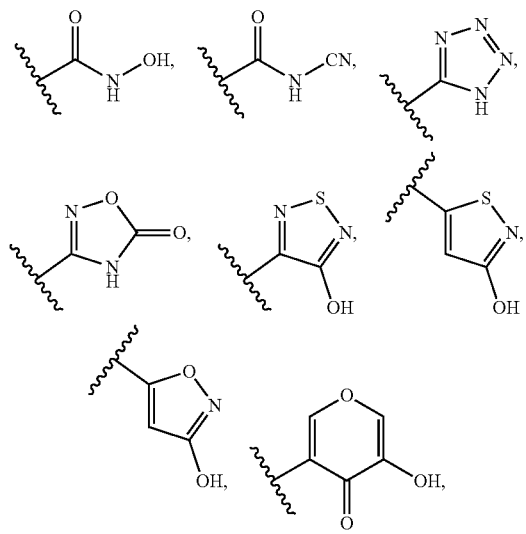

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

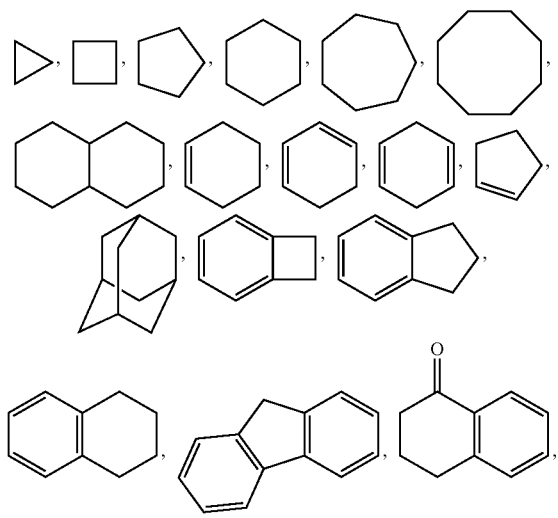

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

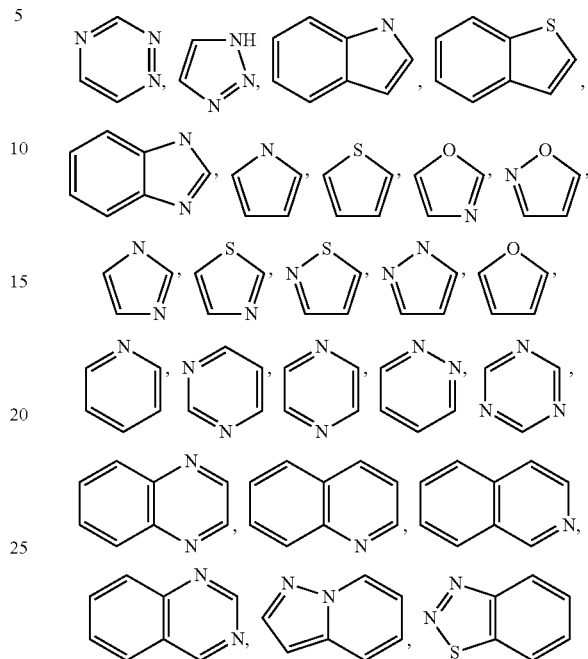

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

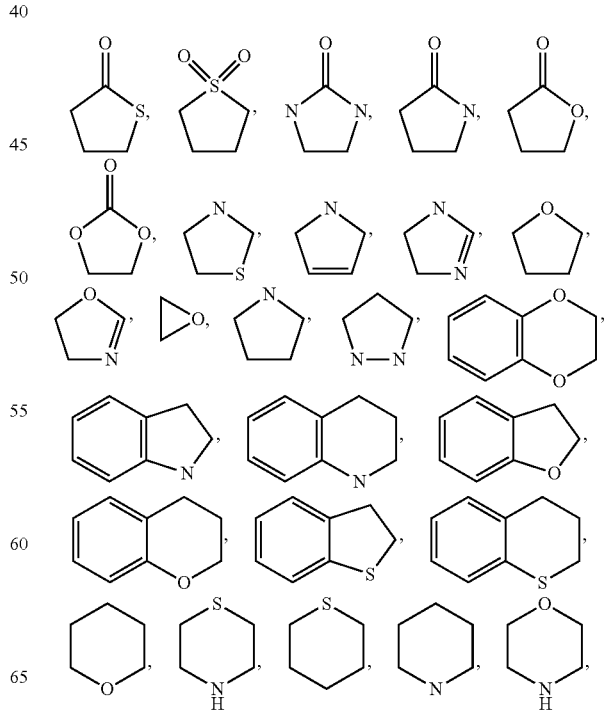

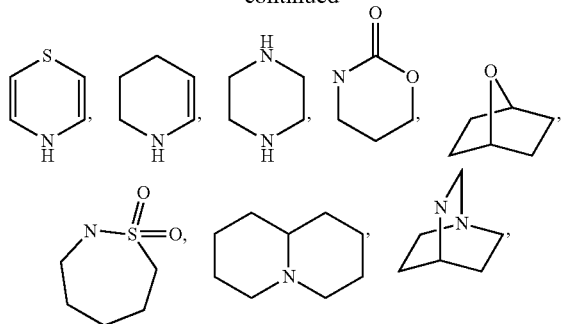

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, —$CF(CH_3)_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

The methods and formulations described herein include the use of crystalline forms (also known as polymorphs), or pharmaceutically acceptable salts of compounds having the structure of Formulas (I), (II), or (III), as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "target protein" refers to a protein or a portion of a protein capable of being bound by, or interacting with a compound described herein, such as a compound of Formulas (I), (II), or (III). In certain embodiments, a target protein is a STIM protein. In certain embodiments, a target protein is an Orai protein.

As used herein, "STIM protein" includes but is not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. (see paragraphs [0211] through [0270] of US 2007/0031814, as well as Table 3 of US 2007/0031814, herein incorporated by reference) As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

As used herein, an "Orai protein" includes Orai1 (SEQ ID NO: 1 as described in WO 07/081804), Orai2 (SEQ ID NO: 2 as described in WO 07/081804), or Orai3 (SEQ ID NO: 3 as described in WO 07/081804). Orai1 nucleic acid sequence corresponds to GenBank accession number NM_032790, Orai2 nucleic acid sequence corresponds to GenBank accession number BC069270 and Orai3 nucleic acid sequence corresponds to GenBank accession number NM_152288. As used herein, Orai refers to any one of the Orai genes, e.g., Orai1, Orai2, Orai3 (see Table I of WO 07/081804). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

The term "fragment" or "derivative" when referring to a protein (e.g. STIM, Orai) means proteins or polypeptides which retain essentially the same biological function or activity in at least one assay as the native protein(s). For example, the fragments or derivatives of the referenced protein maintains at least about 50% of the activity of the native proteins, at least 75%, at least about 95% of the activity of the native proteins, as determined e.g. by a calcium influx assay.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein, "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, and alteration of the kinetics of calcium fluxes into, out of and within cells. In aspect, modulation refers to reduction.

As used herein, the term "target activity" refers to a biological activity capable of being modulated by a modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "inhibits", "inhibiting", or "inhibitor" of SOC channel activity or CRAC channel activity, as used herein, refer to inhibition of store operated calcium channel activity or calcium release activated calcium channel activity.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that one active ingredient, e.g. a compound of Formulas (I), (II), or (III), and a co-agent, are both administered to a patient simultaneously in the form of a single entity or dosage. The term "non-fixed combination" means that one active ingredient, e.g. a compound of Formulas (I), (II), or (III), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of Formula (I), (II), or (III) described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition that includes a compound of Formula (I), (II), or (III) described herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds.

"Bioavailability" refers to the percentage of the weight of the compound disclosed herein (e.g. compound of Formula (I), (II), or (III)), that is delivered into the general circulation of the animal or human being studied. The total exposure (AUC(0-∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound of Formula (I), (II), or (III) disclosed herein, in the plasma component of blood of a subject. It is understood that the plasma concentration of compounds described herein may vary significantly between subjects, due to variability with respect to metabolism and/or possible interactions with other therapeutic agents. In accordance with one embodiment disclosed herein, the blood plasma concentration of the compounds disclosed herein may vary from subject to subject. Likewise, values such as maximum plasma concentration (Cmax) or time to reach maximum plasma concentration (Tmax), or total area under the plasma concentration time curve (AUC(0-∞)) may vary from subject to subject. Due to this variability, the amount necessary to constitute "a therapeutically effective amount" of a compound may vary from subject to subject.

As used herein, "calcium homeostasis" refers to the maintenance of an overall balance in intracellular calcium levels and movements, including calcium signaling, within a cell.

As used herein, "intracellular calcium" refers to calcium located in a cell without specification of a particular cellular location. In contrast, "cytosolic" or "cytoplasmic" with reference to calcium refers to calcium located in the cell cytoplasm.

As used herein, an effect on intracellular calcium is any alteration of any aspect of intracellular calcium, including but not limited to, an alteration in intracellular calcium levels and location and movement of calcium into, out of or within a cell or intracellular calcium store or organelle. For example, an effect on intracellular calcium can be an alteration of the properties, such as, for example, the kinetics, sensitivities, rate, amplitude, and electrophysiological characteristics, of calcium flux or movement that occurs in a cell or portion thereof. An effect on intracellular calcium can be an alteration in any intracellular calcium-modulating process, including, store-operated calcium entry, cytosolic calcium buffering, and calcium levels in or movement of calcium into, out of or within an intracellular calcium store. Any of these aspects can be assessed in a variety of ways including, but not limited to, evaluation of calcium or other ion (particularly cation) levels, movement of calcium or other ion (particularly cation), fluctuations in calcium or other ion (particularly cation) levels, kinetics of calcium or other ion (particularly cation) fluxes and/or transport of calcium or other ion (particularly cation) through a membrane. An alteration can be any such change that is statistically significant. Thus, for example if intracellular calcium in a test cell and a control cell is said to differ, such difference can be a statistically significant difference.

As used herein, "involved in" with respect to the relationship between a protein and an aspect of intracellular calcium or intracellular calcium regulation means that when expression or activity of the protein in a cell is reduced, altered or eliminated, there is a concomitant or associated reduction, alteration or elimination of one or more aspects of intracellular calcium or intracellular calcium regulation. Such an alteration or reduction in expression or activity can occur by virtue of an alteration of expression of a gene encoding the protein or by altering the levels of the protein. A protein involved in an aspect of intracellular calcium, such as, for example, store-operated calcium entry, thus, can be one that provides for or participates in an aspect of intracellular calcium or intracellular calcium regulation. For example, a protein that provides for store-operated calcium entry can be a STIM protein and/or an Orai protein.

As used herein, a protein that is a component of a calcium channel is a protein that participates in multi-protein complex that forms the channel.

As used herein, "basal" or "resting" with reference to cytosolic calcium levels refers to the concentration of calcium in the cytoplasm of a cell, such as, for example, an unstimulated cell, that has not been subjected to a condition that results in movement of calcium into or out of the cell or within the cell. The basal or resting cytosolic calcium level can be the concentration of free calcium (i.e., calcium that is not bound to a cellular calcium-binding substance) in the cytoplasm of a cell, such as, for example, an unstimulated cell, that has not been subjected to a condition that results in movement of calcium into or out of the cell.

As used herein, "movement" with respect to ions, including cations, e.g., calcium, refers to movement or relocation, such as for example flux, of ions into, out of, or within a cell. Thus, movement of ions can be, for example, movement of ions from the extracellular medium into a cell, from within a cell to the extracellular medium, from within an intracellular organelle or storage site to the cytosol, from the cytosol into an intracellular organelle or storage site, from one intracellular organelle or storage site to another intracellular organelle or storage site, from the extracellular medium into an intracellular organelle or storage site, from an intracellular organelle or storage site to the extracellular medium and from one location to another within the cell cytoplasm.

As used herein, "cation entry" or "calcium entry" into a cell refers to entry of cations, such as calcium, into an intracellular location, such as the cytoplasm of a cell or into the lumen of an intracellular organelle or storage site. Thus, cation entry can be, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "protein that modulates intracellular calcium" refers to any cellular protein that is involved in regulating, controlling and/or altering intracellular calcium. For example, such a protein can be involved in altering or adjusting intracellular calcium in a number of ways, including, but not limited to, through the maintenance of resting or basal cytoplasmic calcium levels, or through involvement in a cellular response to a signal that is transmitted in a cell through a mechanism that includes a deviation in intracellular calcium from resting or basal states. In the context of a "protein that modulates intracellular calcium," a "cellular" protein is one that is associated with a cell, such as, for example, a cytoplasmic protein, a plasma membrane-associated protein or an intracellular membrane protein. Proteins that modulate intracellular calcium include, but are not limited to, ion transport proteins, calcium-binding proteins and regulatory proteins that regulate ion transport proteins.

As used herein, "amelioration" refers to an improvement in a disease or condition or at least a partial relief of symptoms associated with a disease or condition.

As used herein, "cell response" refers to any cellular response that results from ion movement into or out of a cell or within a cell. The cell response may be associated with any cellular activity that is dependent, at least in part, on ions such as, for example, calcium. Such activities may include, for example, cellular activation, gene expression, endocytosis, exocytosis, cellular trafficking and apoptotic cell death.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" refers to small soluble proteins secreted by cells that can alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and MIF.

"Store operated calcium entry" or "SOCE" refers to the mechanism by which release of calcium ions from intracellular stores is coordinated with ion influx across the plasma membrane.

"Selective inhibitor of SOC channel activity" means that the inhibitor is selective for SOC channels and does not substantially affect the activity of other types of ion channels.

"Selective inhibitor of CRAC channel activity" means that the inhibitor is selective for CRAC channels and does not substantially affect the activity of other types of ion channels and/or other SOC channels.

Monitoring or Assessing Effects on Intracellular Calcium

In monitoring or assessing the effect of a compound of Formula (I), (II), or (III) on intracellular calcium in any of the screening/identification methods described herein or recognized in the field, a direct or indirect evaluation or measurement of cellular (including cytosolic and intracellular organelle or compartment) calcium and/or movement of ions into, within or out of a cell, organelle, calcium store or portions thereof (e.g., a membrane) can be conducted. A variety of methods are described herein and/or recognized in the field for evaluating calcium levels and ion movements or flux. The particular method used and the conditions employed can depend on whether a particular aspect of intracellular calcium is being monitored or assessed. For example, as described herein in some embodiments, reagents and conditions are used, for specifically evaluating store-operated calcium entry, resting cytosolic calcium levels, calcium buffering and calcium levels and uptake by or release from intracellular organelles and calcium stores. The effect of a compound of Formula (I), (II), or (III) on intracellular calcium can be monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Methods of Modulating Intracellular Calcium

Modulation of intracellular calcium can be any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In particular embodiments, intracellular calcium modulation can involve alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. In some embodiments, modulation of intracellular calcium can involve an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE) in an immune system cell (e.g., a lymphocyte, white blood cell, T cell, B cell), a fibroblast (or a cell derived from a fibroblast), or an epidermal, dermal or skin cell (e.g., a keratinocyte). The step of modulating one or more proteins involved in modulating intracellular calcium (e.g. a STIM protein and/or Orai protein) can involve, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then modulating may involve reducing the level of, expression of, an activity or function of, or a molecular interaction of a protein, e.g. a STIM protein and/or Orai protein.

Examples of Methods of Dosing and Treatment Regimens

The compounds described herein can be used in the preparation of medicaments for the modulation of intracellular calcium, or for the treatment of diseases or conditions that would benefit, at least in part, from modulation of intracellular calcium. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02—about 5000 mg per day, in some embodiments, about 1—about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, about 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compounds of Formulas (I), (II), or (III), and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound of Formulas (I), (II), or (III), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formulas (I), (II), or (III) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Assays

Several techniques may be used to evaluate store operated calcium entry and calcium signaling in cells. Such techniques include, but are not limited to, patch clamp electrophysiology (measurement of calcium ions or other ions across cell membranes, such as plasma membranes), capacitance measurements (allows exocytosis to be followed at the level of single cells), calcium imaging using fluorescent dyes allows patterns of calcium movement within the cytoplasm to be tracked, fluorescence resonance energy transfer (FRET) enables protein-protein interactions to be evaluated, and molecular biology methods allow for the manipulation of the levels of expression of proteins of interest.

A wide variety of assay methods may be used to examine the modulation of intracellular calcium by compounds of Formulas (I), (II), or (III). Such assays include in vitro cell based assays as well as in vivo animal models. Any assays that detect, monitor or measure an effect on intracellular calcium, including calcium entry-mediated events can be used. Such assays include, but are not limited to, assays monitoring, measuring and/or detecting intracellular calcium levels, modulation of calcium levels, and movement of calcium into, out of or within cells and intracellular organelles. Assays can also include monitoring, measuring and/or detecting calcium entry-mediated events and molecules involved in calcium entry-mediated events such as, but not limited to, signal transduction molecules, transcription factors, secreted molecules and other molecules that are affected by changes in calcium homeostasis. Assays include, but are not limited to, those described herein and those described in US patent publication no. 2007/0031814 and WO 07/081804, herein incorporated by reference.

Cells and Cell Models

For in vitro testing of the modulation of intracellular calcium by compounds of Formulas (I), (II), or (III), a wide variety of cell types for such assays are available. In a particular embodiment, the cell is one in which store-operated calcium entry occurs or that can be manipulated such that store-operated calcium entry occurs in the cell. In particular embodiments, the cell contains one or more proteins involved in modulating intracellular calcium (and, in particular, is involved in, participates in and/or provides for store-operated calcium entry, movement of calcium into, out of or within an intracellular organelle or calcium store, modulation of calcium levels in an intracellular organelle or calcium store (e.g., endoplasmic reticulum) and/or calcium buffering), such as those provided herein. In particular embodiments, the protein(s) include STIM proteins (including STIM1, STIM2, DSTIM and CSTIM protein) and/or Orai proteins (Orai1, Orai2, Orai3). The cell may endogenously express the protein(s) or recombinantly express the protein(s).

Cells for use in the methods may be of any species. In one embodiment, the cells can be eukaryotic cells. In one embodiment, the cells can be yeast, insect (e.g., *Drosophila* or *Anopheles*), or mammalian cells. Mammalian cells include, but are not limited to, rodent (e.g., mouse, rat and hamster), primate, monkey, dog, bovine, rabbit and human cells. A variety of cell types can be used in the methods, including, for example, neuronal, nervous system, brain, immune system cells, e.g., T lymphocytes and B cells, primary cells, blood and hematopoietic cells, stromal cells, myeloid cells, lymphoid cells, and a variety of tumor and cancer cells. Particular cells include BV2 cells, *Drosophila* Schneider 2 or S2 cells, human embryonic kidney (HEK293) cells, rat basophilic leukemia (RBL-2H3) cells, Jurkat cells, epithelial cells, rhabdomyosarcoma cells, rhabdoid cells, retinoblastoma cells, neuroepithelioma cells, neuroblastoma cells, osteosarcoma cells, fibroblasts, bone marrow stroma cells, erythroleukemia cells and lymphoblast cells. Other cell lines include HEK 293 and 293T, CHO (including CHO-K1), LTK-, N2A, H6, and HGB. Many such cells and cell lines are available through cell depositories such as, for example, the American Type Culture Collection (ATCC, Manassas, Va.). Primary cells can be obtained by isolation from tissue sources.

Cells from a known cell line can be used, such as neuroblastoma SH-SY5Y cells, pheochromocytoma PC12 cells, neuroblastoma SK-N-BE(2)C or SK-N-SH cells, human SK-N-MC neuroepithelioma cells, SMS-KCNR cells, human LAN-5 neuroblastoma cells, human GI-CA-N neuroblastoma cells, human GOTO neuroblastoma cells, mouse Neuro 2a (N2A) neuroblastoma cells and/or human IMR 32 neuroblastoma cells, chronic myeloid leukemia cells (e.g., human K562 cells), promyelocytic leukemia cells (e.g., HL60 cells) and histiocytic lymphoma cells (e.g., U937 cells), Burkitt's lymphoma cells (e.g., CA46 cells), B-cells (e.g., NALM6), acute lymphoblastic leukemia cells (e.g., MOLT4 cells), T cells (e.g. Jurkat cells) and early T-ALL (e.g., DU528) cells.

In one embodiment, it may be desirable to utilize a cell that contains components of signaling and messenger systems that can effect release of calcium from intracellular stores. For example, cells containing components of receptor-mediated phospholipase C (PLC) activation systems can be used for physiological activation (via generation of $IP_3$) of store depletion to facilitate monitoring of store-operated calcium entry. Receptor-mediated PLC activation occurs through distinct coupling mechanisms: PLC-β activation by G protein-coupled receptors (GPCRs) and PLC-γ activation by tyrosine kinase receptors and nonreceptor tyrosine kinases. Thus, cells containing a receptor-mediated PLC-activation system can be monitored or assessed for store-operated calcium entry upon agonist activation of one or more receptors known to participate in the system. (see e.g. Bouron (2000) FEBS Lett 470:269-272; Millar et al. (1995) *J. Exp. Biol.* 198:1843-1850; Yagodin et al. (1998) *Cell Calcium* 23:219-228; Yagodin et al. (1999) *Cell Calcium* 25:429-438; and Patterson et al. (2002) *Cell* 111:1-20).

Evaluation of Store-Operated Calcium Entry

In one aspect, compounds described herein are added to cells under conditions that permit store-operated calcium entry to occur in order to assess the effects of Formulas (I), (II), or (III) on store-operated calcium entry. Such conditions are described herein and are recognized in the field.

For example, in one method cells may be treated to reduce the calcium levels of intracellular calcium stores and then analyzed for evidence of ion (e.g., calcium) influx in response thereto in the presence of a compound described herein. Techniques for reducing calcium levels of intracellular stores and for analyzing cells for evidence of ion (e.g., calcium) influx are recognized in the field and described herein.

In other methods, electrophysiological analysis of currents across a cell-detached plasma membrane patch or an outside-out membrane vesicle may be used to detect or monitor store-operated channel currents (e.g., $I_{SOC}$, $I_{CRAC}$) in the presence of a compound described herein.

Evaluation of Calcium Entry-Mediated Events

A number of molecules involved in calcium-regulated pathways are known. Evaluation of molecules involved in calcium-entry mediated events can be used to monitor intracellular calcium, and can be used, for example in screening assays described herein to monitor the effects of the compounds presented herein. Examples of assays include but are not limited to assays which detect, or determine the presence, levels, alteration of levels, production, modification (such as phosphorylation and dephosphorylation), translocation, degradation and activity of molecules involved in calcium-entry mediated events (see for example, Trevillyan et al. (2001) *J. Biol. Chem.* 276:48118-26). The assays described herein can be used with cells that have been treated with or contacted with a compound presented herein, or that express an altered amount of a test molecule (such as a protein involved in calcium regulation, including a STIM protein, Orai protein), or with control cells. The assays can also be conducted in cells that have been stimulated with a physiological or non-physiological activator, or in unstimulated cells. The following are representative assays for molecules involved in calcium-entry mediated events and are meant to be exemplary only. Other assays for these molecules and assays for other molecules involved in calcium-entry mediated events can also be employed in any of the screening and/or modulation methods described herein.

β-Hexosaminidase Release

In mast cells, $Ca^{2+}$ influx results in degranulation and release of inflammatory mediators such as heparin, histamine and enzymes such as β-hexosaminidase. Detecting and/or measuring release of such molecules can thus be used to monitor intracellular calcium. For example, media from mast cells can be collected. A suitable substrate for β-hexosaminidase (e.g. p-nitrophenyl-acetyl-glucosamide) can then be added and the absorbance of the resulting mixture assessed to measure the relative amount of β-hexosaminidase activity in the samples (Funaba et al. (2003) *Cell Biol. International* 27:879-85).

Calcium/Calmodulin-Dependent CaN Phosphatase Activity

The phosphatase calcineurin (CaN) dephosphorylates various proteins, affecting their activity and localization. CaN activity can be assessed by incubating purified CaN and a CaN substrate, for example a radiolabeled peptide corresponding to a sequence in the RII subunit of cAMP-dependent kinase, either with or without a compound of Formulas (I), (II), or (III) (see, Trevillyan et al. (2001) *J. Biol. Chem* 276:48118-26). The level of radiolabeled peptide and/or the amount of free inorganic phosphate released can be measured to assess CaN dephosphorylation activity.

NFAT Transcriptional Activity

The NFAT (nuclear factor of activated T cells) transcription factor regulates a number of genes in response to intracellular calcium levels. For example, NFAT proteins regulate the transcription of cytokine genes involved in the immune response. Promoters from NFAT-regulated genes, and/or regulatory regions and elements from these genes, can be used to monitor NFAT regulated expression and thereby monitor intracellular calcium. Reporter gene fusions can be constructed with NFAT regulated promoters or NFAT-regulated elements operably linked to a reporter gene such as luciferase, β-galactosidase, green fluorescent protein (GFP) or any other known reporter in the art (see for example, Published U.S. Application no. 2002-0034728). The amount of reporter protein or activity is a measure of NFAT activity.

NFAT Phosphorylation

NFAT activation is regulated primarily through its phosphorylation, which in turn regulates its subcellular localization. In unstimulated cells, NFAT is a hyperphosphorylated cytosolic protein. An elevation in intracellular $Ca^{2+}$, induced by a variety of mechanisms, increases the activity of the $Ca^{2+}$-calmodulin-dependent phosphatase, calcineurin. Activated calcineurin dephosphorylates multiple serine residues within the regulatory region of the NFAT molecule. NFAT is rephosphorylated in response to decreases in $Ca^{2+}$ levels or CaN inhibition.

The phosphorylation state of NFAT can be monitored for example, by expressing a detectably tagged NFAT protein in cells, such as a His6 tagged-NFAT. Tagged NFAT can be purified from cells using $Ni^{2+}$ chromatography and subjected to gel electrophoresis and staining or western blotting. More highly phosphorylated forms of NFAT can be distinguished by their slower migration. The state of phosphorylated NFAT can be used as a measure of NFAT activation (see, Trevillyan et al. (2001) *J. Biol. Chem* 276:48118-26).

NFAT Nuclear Localization

NFAT localization between the cytoplasm and nucleus is regulated by the phosphorylation state of NFAT. Phosphorylation of NFAT prevents nuclear localization by masking the nuclear localization sequence. NFAT nuclear localization can be monitored, for example, by expressing fluorescently tagged NFAT, for example, GFP-NFAT, in cells. Confocal microscopy can be used to monitor nuclear localization of the tagged NFAT (see, Trevillyan et al. (2001) *J. Biol. Chem* 276:48118-26).

Cytokine Secretion

Cytokine secretion, such as IL-2 secretion, can be monitored using protein detection assays. For example, supernatant can be collected from immune cells. An ELISA assay or other suitable format with IL-2 antibodies can be used to detect and/or measure the amount of IL-2 secreted as compared to control cells. Secretion of other cytokines, for example, TNF-α, can also be detected in similar assays.

Cytokine Expression

Expression of cytokines, such as, but not limited to IL-2, can be assessed either directly or indirectly in cells. For example, in indirect methods, an IL-2 promoter can be operably linked to a reporter gene such as luciferase or β-galactosidase, and the reporter construct introduced into cells. Reporter gene expression can be monitored and compared to gene expression in control cells (see, Trevillyan et al. (2001) *J. Biol. Chem* 276:48118-26). Alternatively, expression of endogenous or recombinant IL-2 mRNA or protein can be assessed.

T Cell Proliferation

Cytokines such as IL-2 are necessary for T-cell proliferation in response to mitogen or alloantigen stimulation, and thus T-cell proliferation is altered by changes in cytokine expression or secretion. T cells can be induced, such as with concanavalin A or alloreactive lymphocytes and T cell proliferation measured, for example, by subjecting cells to a pulse of $^3$H-thymidine and measuring $^3$H-thymidine incorporation (see, Trevillyan et al. (2001) *J. Biol. Chem* 276:48118-26).

In some embodiments, the modulation (e.g. inhibition or reduction) of SOCE by compounds presented herein are determined by evaluation of any of the following criteria:

a. there is direct inhibition of increased [Ca$^{2+}$]i as measured by a calcium indicator;
b. there is a direct inhibition of I$_{SOC}$ or I$_{CRAC}$ as measured by patch clamp;
c. there is inhibition of downstream signaling functions such as calcineurin activity, NFAT subcellular localization, NFAT phosphorylation, and/or cytokine, e.g., IL-2, production; or
d. there are modifications in activation-induced cell proliferation, differentiation and/or apoptotic signaling pathways.

Animal Models

Animal models that can be used in embodiments of the methods further include animals, such as, but not limited to non-human animals, which have, in at least some of their cells, an alteration or defect in, or aberrant functioning of, a cellular process which relies on or is regulated by intracellular calcium. Cellular processes that rely on or are regulated by intracellular calcium include, for example, cellular activation, gene expression, cellular trafficking, and apoptosis. Diseases/disorders that involve defects that may be at least partially compensated for by modulation of intracellular calcium include, but are not limited to: autoimmune disorders, including rheumatoid arthritis, inflammatory bowel disease, Sjogren's syndrome (cytokines associated with lymphocyte invasion of salivary epithelial cells can reduce calcium mobilization in parotid cells; also, T-cell activation, including activation of transcription factors, cytokine gene expression and cell proliferation, depends on sustained elevation of intracellular calcium level provided by store-operated calcium influx), asthma (store-operated calcium entry may play an important role in mediating bronchial constriction and bronchial smooth muscle cell proliferation), glomerulonephritis and glomerular inflammation (changes in intracellular calcium, such as by store-operated calcium entry, signal monocyte adhesion in a co-culture model of glomerular inflammation).

Types of animal models include, but are not limited to, non-human animals, such as non-human invertebrates and vertebrates and non-human mammals, rodents (e.g., mice, rat and hamster), cows, chickens, pigs, goats, dogs, sheep, insects, *Drosophila*, nematodes, worms, *C. elegans*, monkeys, gorillas, and other primates.

Animal models include transgenic and non-transgenic animals. One example of such an animal model that can be used in particular embodiments of the methods is a rodent model of airway hyperresponsiveness (AHR), a characteristic of asthma. This model can be generated, for example, by sensitization through immunization with ovalbumin followed by exposure to aerosolized ovalbumin and challenge by cholinergic stimulation (e.g., via administration of methacholine or acetylcholine) (see, e.g., Xu et al. (2002) *J. Appl. Physiol.* 93:1833-1840; Humbles et al (2002) *Proc. Natl. Acad. Sci.* 99:1479-1484). Airway hyperresponsiveness (which can be evaluated using methods, such as for e.g., using barometric plethysmography to record respiratory pressure curves and through measurement of pulmonary parameters such as pulmonary conductance and pulmonary compliance) can be assessed and compared in animals treated and not treated with a compound presented herein. A further example of an animal model that can be used in particular embodiments of the methods is a rodent model of mesangial proliferative glomerulonephritis, which can be generated, for example, by administration of anti-Thy1.1 antibody (see, e.g., Jefferson and Johnson (1999) *J. Nephrol.* 12:297-307). Any number of parameters indicative of glomerulonephritis or renal dysfunction (e.g., mesangial cell proliferation, blood pressure, urinary protein excretion, creatinine clearance, glomerulosclerosis index and other parameters) can be evaluated and compared in animals treated with and not treated with test agent. The non-obese diabetic (NOD) mouse, an inbred mouse strain that spontaneously develops autoimmune diabetes that shares many immunogenetic features with Type 1 diabetes mellitus, is another example of an animal model that can be used in a particular embodiment of the methods. These mice also manifest many characteristics of autoimmune exocrinopathy (such as Sjorgen's syndrome) including declining exocrine tissue secretory function (see, e.g., Humphreys-Beher and Peck (1999) *Arch. Oral Biol.* 44 Suppl 1:S21-25 and Brayer et al. (2000) *J Rheumatol.* 27:1896-1904). Characteristics relevant to Sjorgen's syndrome (e.g., lymphocytic infiltrates in exocrine glands (e.g., salivary and lacrimal glands), presence of dendritic cells and macrophages in submandibular glands, integrity of the lacrimal gland by measurement of basal and stimulated tear secretion, saliva flow rates and amylase activity) can be evaluated and compared in animals treated with and not treated with a compound described herein. An animal (e.g., rodent) model of autoimmune disease can also be used in particular embodiments of the methods. Such animals include rat models available through the National Institutes of Health (NIH) Autoimmune Rat Model Repository and Development Center (Bethesda, Md.; accessible at www.ors.od.nih.gov/dirs/vrp/ratcenter). One rat model of rheumatoid arthritis (RA) and related chronic/inflammatory autoimmune diseases is the collagen-induced arthritis (CIA) model (see, e.g., Griffiths and Remmers (2001) *Immunol. Rev.* 184:172-183). Characteristic phenotypes of autoimmune disease (e.g. altered levels of immune reactivity to self-antigens, chronic inflammation of autoantigen-expressing target organs, and activation and participation of invading mononuclear cells and tissue fibroblasts in organ damage) can be evaluated and compared in animals treated with and not treated with a compound presented herein. An animal (e.g., rodent) model of neuropathic or inflammatory pain can also be used in a particular embodiment of the methods. For example, one rat model of neuropathic pain involves development of tactile allodynia (exaggerated response to otherwise innocuous stimuli) after ligation of lumbar spinal nerves (see, e.g., Chaplan et al. (1994) *J. Neurosci. Methods* 53:55-63 and Luo et al. (2001) *J. Neurosci.* 21:1868-1875). Tactile allodynia, one characteristic feature of neuropathic pain, can be evaluated (e.g., by evaluating paw withdrawal threshold in response to application of pressure) and compared in animals treated and not treated with a compound described herein.

EXAMPLES

These examples are provided for illustrative purposes only and not to limit the scope of the claims provided herein.
In Vitro Evaluation Fluorescence-based A neuron cell line (Neuro-2A, N-2A) was either cultured alone or in co-culture with microglial BV2 cells. Cells were exposed to a cycle of 2 h oxygen glucose deprivation (OGD) plus 22 h reoxygenation in the absence or presence of inhibitor (concentrations 1-50 μM). Cell viability was determined using quantitative calorimetric MTT assay and live/dead assay using immunofluorescence imaging. Toll-like receptor (TLR)-3 and -4 agonists induced inflammatory responses in microglia leading to increased nitric oxide (NO) generation as determined by the Greiss reagent. Intracellular calcium was determined by live fluorescence microscopy using a calcium fluorescent probe. Peroxide levels were measured as an indicator of oxidative stress. CRAC channels proteins (STIM1 & ORAI1), phosphoactive stress kinase JNK1/2, iNOS and expression was determined by immunoblotting assays. NFκB, NFAT and CREB transcription factors activation was measured by phosphorylation and nuclear translocation. Western blots revealed the presence of the canonical CRAC channel proteins STIM1 and ORAI1 in brain derived microglia BV2 cells. CRAC inhibition dose dependently decreased NO release and inflammatory proteins iNOS and COX-2 expression in activated microglia, but did not affect STIM1 or ORAI1 expression. The functional activity of the CRAC channels was evaluated by the effect on intracellular calcium accumulation in BV2 cells. Basal cytoplasmic levels of calcium were elevated by both TLR-3 and -4 agonists compared to controls, and CRAC channel inhibition abrogated this increase. TLR-4 agonist induced JNK1/2 kinase and nuclear factor CREB activation, and these were also attenuated by inhibitor treatment, while NF-κB and NFAT were not (n=1, need to repeat to confirm). OGD significantly decreased N2A neuronal cell viability, which was further exacerbated by BV2 cells. OGD-induced neurotoxic changes in mono and co-cultures were inhibited by the CRAC channel inhibitor (n=3-5, *p<0.05). The data shows that CRAC channel inhibition confers a neuroprotective effect through decrease of oxidative stress and exerts potent blockade of microglia mediated calcium influx, and inflammatory protein gene expression mediated at least in part through JNK and transcription factor CREB signaling pathways which suggests a novel anti-inflammatory approach for treating ischemic stroke.

What is claimed is:

1. A method for treating stroke or traumatic brain injury in an individual in need thereof comprising administering to the individual a therapeutically effective amount of a compound having the structure of Formula (II):

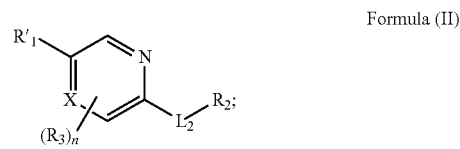

Formula (II)

wherein:

$R'_1$ is

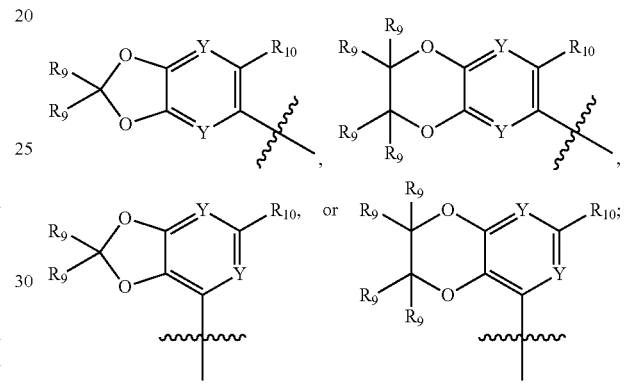

$L_2$ is —NH—C(=O)—, or —C(=O)NH—;

X is $CR_3$ or N;

Y is independently selected from $CR_9$ or N;

$R_2$ is $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, $C_1$-$C_4$alkylene$C_2$-$C_8$heterocycloalkyl, aryl, heteroaryl, fused aryl or fused heteroaryl; wherein $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, $C_1$-$C_4$alkylene$C_2$-$C_8$heterocycloalkyl, aryl, heteroaryl, fused aryl or fused heteroaryl is optionally substituted with at least one $R_3$;

$R_3$ is independently selected from H, F, D, Cl, Br, I, —CN, —$NO_2$, —OH, —$CF_3$, —$OCF_3$, —$OR_5$, $C_1$-$C_6$alkyl, $C_3$-$C_8$cycloalkyl, $C_1$-$C_6$heteroalkyl, $C_1$-$C_6$haloalkyl, $C_2$-$C_5$heterocycloalkyl, optionally substituted aryl, optionally substituted O-aryl, optionally substituted heteroaryl, n is an integer selected from 0-2;

$R_9$ is independently selected from H, D, halogen, $C_1$-$C_6$alkyl, $C_1$-$C_6$haloalkyl, —$OR_5$, —$OCF_3$, $C_1$-$C_6$ carbonylalkyl, or —$CF_3$; or two $R_9$ attached to the same carbon atom form an oxetane ring;

$R_{10}$ is selected from halogen, $C_1$-$C_6$alkyl, $C_1$-$C_6$haloalkyl, —$OR_5$, —$OCF_3$, $C_1$-$C_6$ carbonylalkyl, or —$CF_3$;

$R_5$ is independently selected from H, $C_1$-$C_6$alkyl, $C_1$-$C_6$haloalkyl, $C_3$-$C_8$cycloalkyl, phenyl, and benzyl;

or a pharmaceutically acceptable salt thereof.

2. The method of claim 1 wherein X is CH.

3. The method of claim 1 wherein $R'_1$ is

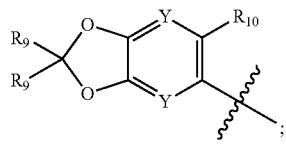

and Y is CH.

4. The method of claim 3 wherein $R_2$ is phenyl substituted with at least one $R_3$.

5. The method of claim 4 wherein at least one $R_3$ is selected from Cl, Br, F, I, $CF_3$, $C_1$-$C_6$alkyl, or $OC_1$-$C_6$alkyl.

6. The method of claim 5 wherein at least one $R_3$ is selected from Cl, F, and $CH_3$.

7. The method of claim 3 wherein $R_2$ is phenyl substituted with at least one F.

8. The method of claim 7 wherein at least one $R_9$ is a halogen.

9. The method of claim 1 wherein $R'_1$ is

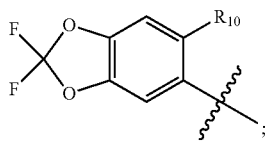

and n is 0.

10. The method of claim 9 wherein $R_{10}$ is a halogen or $C_1$-$C_6$alkyl.

11. The method of claim 10 wherein $R_{10}$ is Cl.

12. The method of claim 10 wherein $R_{10}$ is —$CH_3$.

13. The method of claim 10 wherein $R_{10}$ is —$CH_2CH_3$.

14. The method of claim 1 wherein $R_2$ is phenyl substituted with two $R_3$, wherein one $R_3$ is F and one $R_3$ is $CH_3$.

15. The method of claim 1 wherein $R_2$ is phenyl substituted with two $R_3$, wherein each $R_3$ is F.

16. The method of claim 1 wherein $R_2$ is phenyl substituted with three $R_3$, wherein each $R_3$ is F.

17. The method of claim 1 wherein $R_2$ is heteroaryl substituted with at least one $R_3$.

18. The method of claim 17 wherein heteroaryl is pyridyl.

19. The method of claim 17 wherein $R_2$ is heteroaryl substituted with at least one $R_3$ selected from Cl, Br, F, I, $CF_3$, $C_1$-$C_6$alkyl, or $OC_1$-$C_6$alkyl.

20. The method of claim 1 wherein $L_2$ is —NH—C(=O)—.

* * * * *